United States Patent
Hutcheson et al.

(10) Patent No.: US 11,612,601 B1
(45) Date of Patent: Mar. 28, 2023

(54) TARGETING EPIDERMAL GROWTH FACTOR TO TREAT VASCULAR CALCIFICATION

(71) Applicants: Joshua Hutcheson, Miami, FL (US); Amirala Bakhshiannik, Miami, FL (US); Hooi Hooi Ng, Miami, FL (US)

(72) Inventors: Joshua Hutcheson, Miami, FL (US); Amirala Bakhshiannik, Miami, FL (US); Hooi Hooi Ng, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/590,401

(22) Filed: Feb. 1, 2022

(51) Int. Cl.
*A61K 31/517* (2006.01)
*A61P 9/10* (2006.01)

(52) U.S. Cl.
CPC .............. *A61K 31/517* (2013.01); *A61P 9/10* (2018.01)

(58) Field of Classification Search
CPC ................................ A61K 31/517; A61P 9/10
See application file for complete search history.

(56) References Cited

PUBLICATIONS

Tani, T., "Development of a novel chronic kidney disease mouse model to evaluate the progression of hyperphosphatemia and associated mineral bone disease." Scientific reports 7.1 (2017): 1-12.*
Grossmann, C., "Aldosterone-induced EGFR expression: interaction between the human mineralocorticoid receptor and the human EGFR promoter." American Journal of Physiology—Endocrinology and Metabolism 292.6 (2007): E1790-E1800.*
Gao, J., "Roles of aldosterone in vascular calcification: an update." European Journal of Pharmacology 786 (2016): 186-193.*
Weglicki, W. B., "The EGFR tyrosine kinase inhibitor tyrphostin AG-1478 causes hypomagnesemia and cardiac dysfunction." Canadian journal of physiology and pharmacology 90.8 (2012): 1145-1149.*
Barrick, C. J. "Chronic pharmacologic inhibition of EGFR leads to cardiac dysfunction in C57BL/6J mice." Toxicology and applied pharmacology 228.3 (2008): 315-325.*
Barrick, C. J.,"Reduced EGFR causes abnormal valvular differentiation leading to calcific aortic stenosis and left ventricular hypertrophy in C57BL/6J but not 129S1/SvlmJ mice." American Journal of Physiology—Heart and Circulatory Physiology 297.1 (2009): H65-H75.*
Nik, Amirala Bakhshian et al. "Epidermal Growth Factor Receptor Inhibition Prevents Caveolin-1-dependent Calcifying Extracellular Vesicle Biogenesis," bioRxiv preprint doi: https://doi.org/10.1101/2021.11.08.467799; this version posted Nov. 8, 2021.

* cited by examiner

*Primary Examiner* — John M Mauro
(74) *Attorney, Agent, or Firm* — Saliwanchik, Lloyd & Eisenschenk

(57) ABSTRACT

The subject invention provides compositions and methods for treating, preventing or ameliorating vascular calcification, for example, medial vascular calcification and intimal atherosclerotic calcification via the inhibition of EGFR. The subject invention also provides compositions and methods for treating or preventing a disease associated with vascular calcification via the inhibition of EGFR.

20 Claims, 11 Drawing Sheets

Specification includes a Sequence Listing.

A

B

C

D

E

F

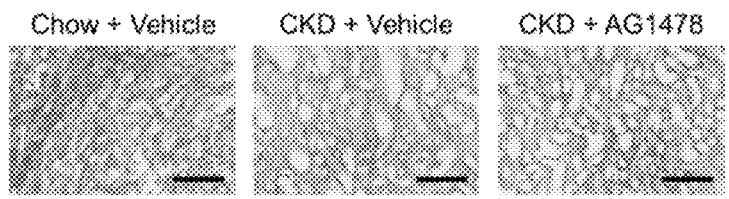
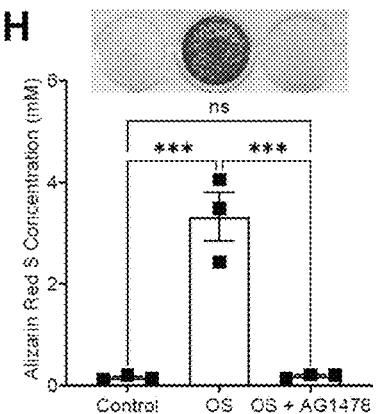
FIG. 1G
FIG. 1H
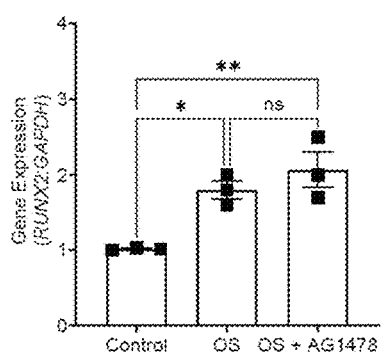
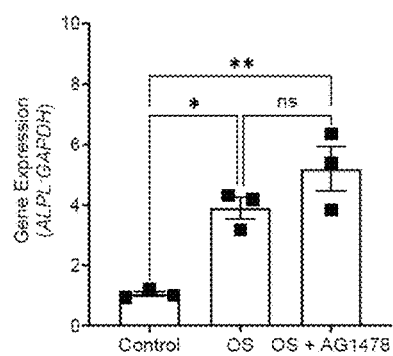
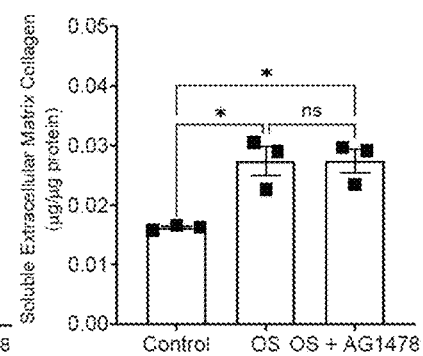
FIG. 1I
FIG. 1J
FIG. 1K

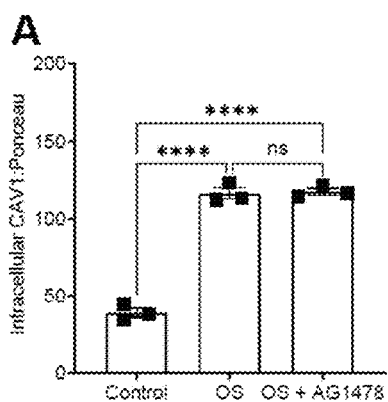
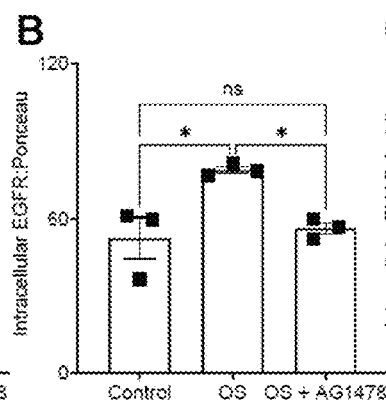
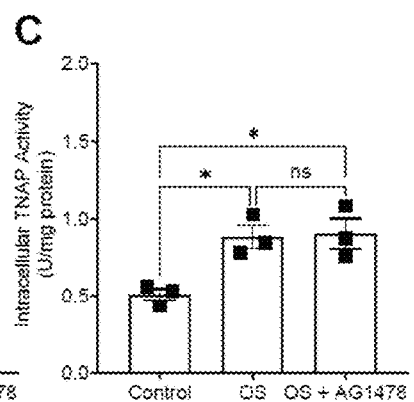
FIG. 2A　　　　　　FIG. 2B　　　　　　FIG. 2C
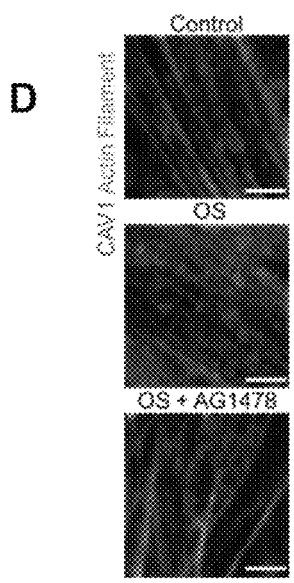
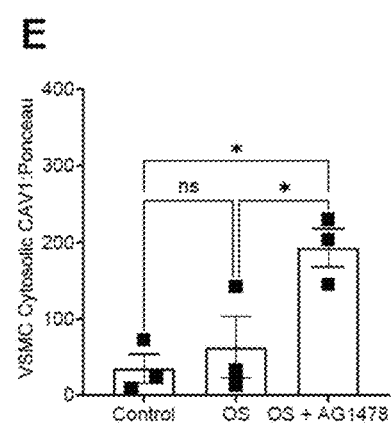
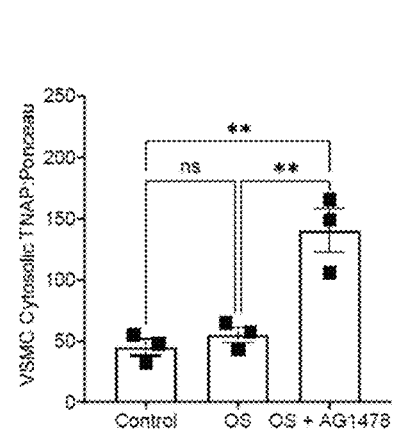
FIG. 2D　　　　　　FIG. 2E　　　　　　FIG. 2F

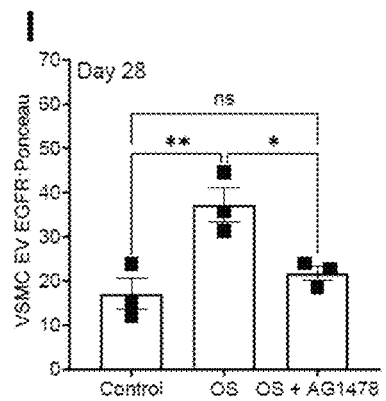
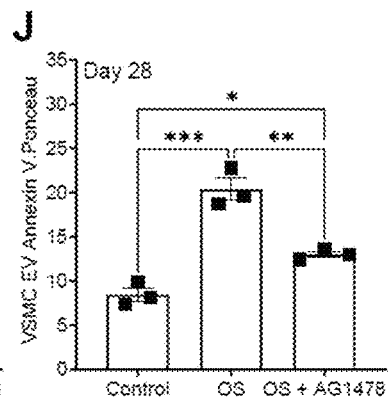
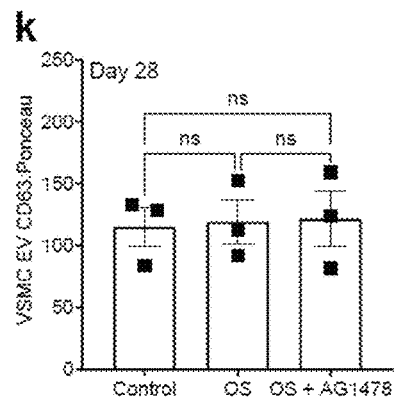
FIG. 2I  FIG. 2J  FIG. 2K
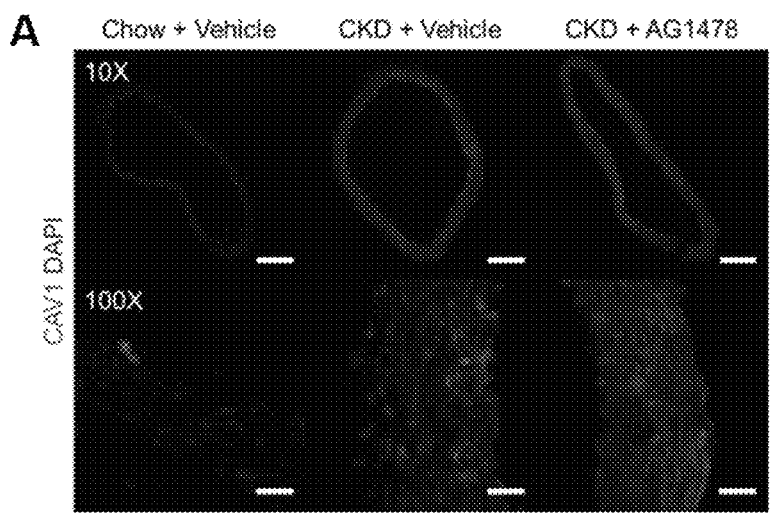
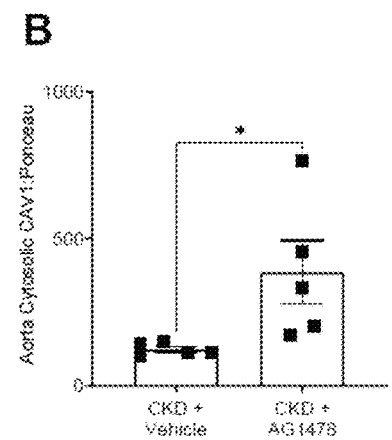
FIG. 3A  FIG. 3B

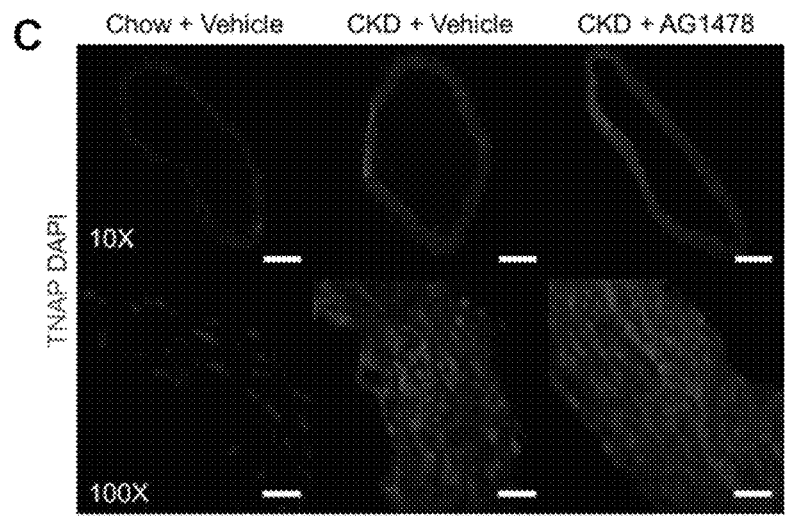
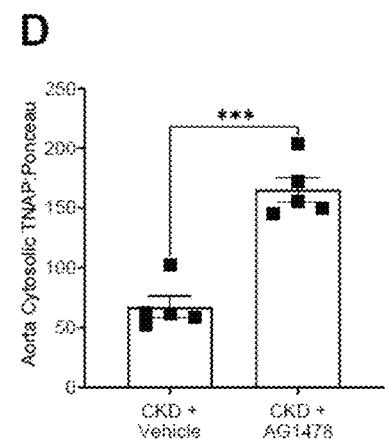
FIG. 3C
FIG. 3D
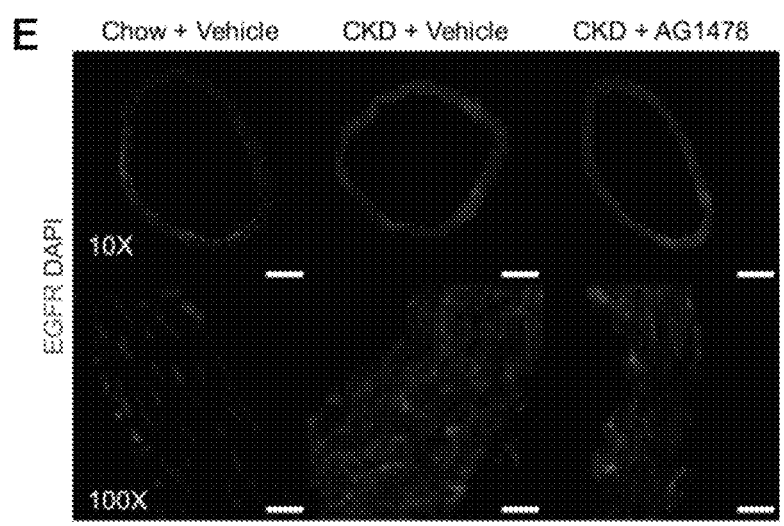
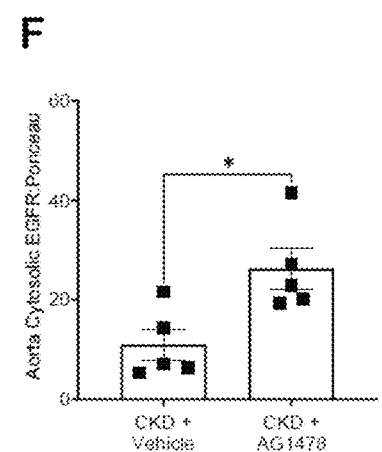
FIG. 3E
FIG. 3F

H
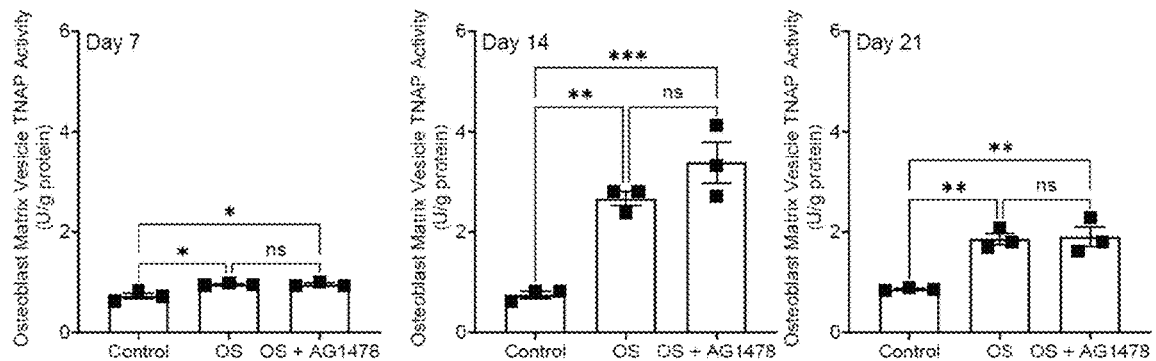
FIG. 4H
FIG. 5A
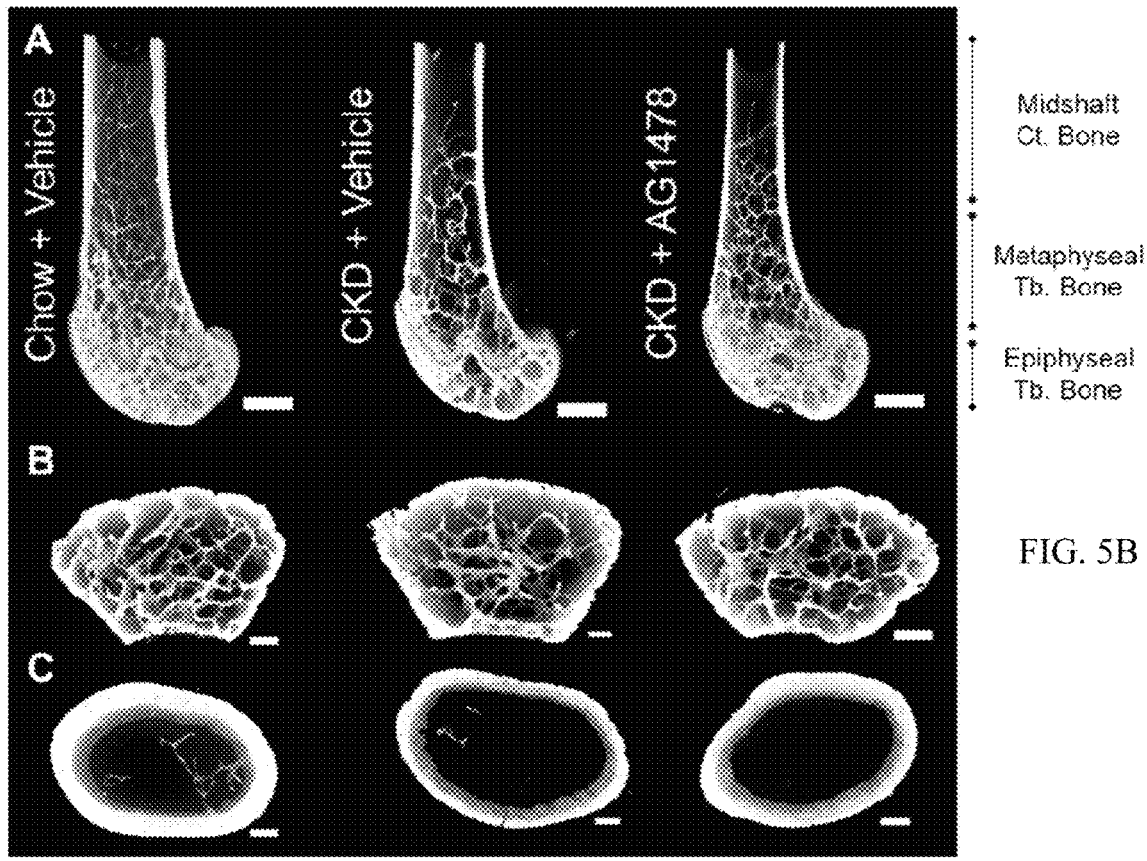
FIG. 5B
FIG. 5C

TARGETING EPIDERMAL GROWTH FACTOR TO TREAT VASCULAR CALCIFICATION

SEQUENCE LISTING

The Sequence Listing for this application is labeled "SeqList-01Feb22_ST25.txt," which was created on Feb. 1, 2022, and is 3 KB. The Sequence Listing is incorporated herein by reference in its entirety.

BACKGROUND

Medial calcinosis manifests as the formation of the calcium phosphate mineral in the arterial media of the vessel walls, leading to vascular stiffening, dysfunction, and cardiac overload. Medial calcinosis highly correlates with cardiovascular morbidity and mortality. Calcification of arterial media commonly occurs in patients with chronic kidney disease (CKD). CKD patients with no detectable vascular calcification have 8-year all-cause survival rates of around 90% compared to 50% survivability in age-matched patients with medial calcification. Imbalanced serum calcium and phosphorous levels elevate the risk of medial calcinosis in CKD patients. Impaired renal excretion of phosphorous also leads to abnormal bone remodeling and mediates osteogenic differentiation of vascular smooth muscle cells (VSMCs) in the vessel walls.

Types of vascular calcification include, for example, calcific atherosclerosis, calcific medial vasculopathy, elastocalcinosis, calcific uremic arteriolopathy, calcific aortic valvular stenosis, and portal vein calcification. Vascular calcification is associated with a range of diseases, such as atherosclerosis, hyperlipidemia, osteoporosis, hypertension, inflammation, diabetes (e.g., type 2 diabetes mellitus (T2DM)), end-stage renal disease (ESRD), hyperphosphatemia, amputation, vitamin D disorders, vitamin K deficiency, Kawasaki disease, pseudoxanthoma elasticum (PXE), Marfan's Syndrome, Singleton-Merten syndrome, β-thalassemia, rheumatoid arthritis, congenital bicuspid valve, rheumatic heart disease, and liver disease.

Osteogenic differentiation of resident VSMCs, and release of calcifying extracellular vesicles (EVs) mediate nucleation and growth of ectopic vascular calcification. This process mimics aspects of the physiological mineralization of osteoblasts and chondrocytes in bone via release of matrix vesicles. Although calcifying EVs released into the vascular wall and bone matrix vesicles contribute to similar endpoints of mineralization, they originate through different pathways. The development of pharmaceuticals for vascular calcification targeting mechanisms specific to vascular calcifying EVs could avoid deleterious off-target effects on bone. Formation of calcifying EVs by VSMCs requires caveolin-1 (CAV1), a scaffolding membrane protein. CAV1 resides in caveolar domains, small invaginations (50-100 nm) on the plasma membrane, which consist of the caveolin protein family, cholesterol, sphingolipids, and receptors. Caveolar functions include intra/extracellular lipid transfer, endocytosis, mechanotransduction, and signaling mediation. Calcifying VSMCs release CAV1-enriched EVs, and CAV1 knockdown abrogates calcification in these cells.

Epidermal growth factors (EGFs) are signaling proteins that control a wide range of cellular functions critical for intercellular communication and tissue homeostasis. EGF Receptor (EGFR) is a cell surface receptor with downstream receptor tyrosine kinase (RTK) activity, which binds multiple EGF ligands, and fibroblast growth factor 21 (FGF21), and has multiple functions that modulate vascular SMCs, cardiomyocytes, cardiac fibroblasts, endothelial cells (ECs), adipocytes, and immune cells.

EGFR is a tyrosine kinase transmembrane glycoprotein, which localizes abundantly in caveolar domains. EGFR and its ligands are expressed in the vascular system by, for example, SMCs and ECs, and can regulate their proliferation, migration, survival, and production of angiogenic factors and reactive oxygen species. Overexpression of EGFR promotes gene amplification and mutation consequence in cell proliferation, survival, invasion, metastasis, and tumor induced neoangiogenesis. EGFR and EGF signaling also promotes vascular abnormalities including abdominal aortic aneurysm formation, cardiac remodeling, endothelial dysfunction, fibrosis, hypertension, and neointimal hyperplasia.

EGFR interacts with and modulates CAV1 trafficking and recruits signaling proteins to caveolar domains. EGFR actively participates in human cancer progression, and EGFR tyrosine kinase inhibition has become a widely utilized strategy in cancer therapies. Both CAV1 and EGFR are elevated during breast cancer progression, and clinical studies indicate that overexpression of EGFR in breast cancer associates with increased ectopic calcification. In cardiovascular pathogenesis, elevated EGFR activity correlates with oxidative stress and chronic inflammation. EGFR inhibition in apolipoprotein E-deficient mice fed a high-fat diet prevented atherosclerotic plaque development. However, the role of EGFR in VSMC-mediated calcification has not been reported.

There are currently no effective pharmacotherapies to prevent or treat vascular calcification. Conventional therapeutic approaches may involve controlling serum phosphate while minimizing oral calcium load, for example, through a use of an adapted dialysate calcium concentration; use of phosphate-binding agents; the administration of calcitriol or vitamin D analogues; the use of calcimimetics; diet recommendations (reducing dietary phosphate intake and administering phosphate binders and calcium supplements); and/or the uptake of native vitamin D supplements.

Thus, there is a need for the identification of drugs for treating and preventing vascular calcification, in particular, via the inhibition of EGFR. There is a further need for developing methods for treating and preventing diseases associated with vascular calcification, e.g., medial vascular calcification or intimal atherosclerotic calcification.

BRIEF SUMMARY

The subject invention provides compositions and methods for treating, preventing and/or ameliorating vascular calcification, for example, medial vascular calcification or intimal atherosclerotic calcification. The subject invention also provides compositions and methods for treating or preventing a disease associated with vascular calcification.

In one embodiment, the methods of the subject invention employ epidermal growth factor receptor (EGFR)-based strategies for treating, preventing and/or ameliorating vascular calcification and diseases associated with vascular calcification. The EGFR inhibitors and compositions comprising EGFR inhibitors affect and control the mechanism by which extracellular vesicles (EVs) in smooth muscle cells (SMCs) obtain their mineralizing properties for vascular calcification.

In one embodiment, the methods of the subject invention are for treating, preventing and/or ameliorating cardiovascular calcification. In other embodiments, the method is for treating, preventing and/or ameliorating Mönckeberg's arteriosclerosis, calcific atherosclerosis, calcific medial vasculopathy, elastocalcinosis, aalcific aortic valvular stenosis, portal vein calcification and/or calcific uremic arteriolopathy (CUA).

In one embodiment, the subject invention provides a method for preventing and/or treating vascular calcification via the inhibition of EGFR, the method comprising administering to a subject in need of such prevention and/or treatment a pharmaceutical composition comprising one or more EGFR inhibitors. In preferred embodiments, the administration is local, oral, transdermal, or parenteral administration.

EGFR inhibition prevents/treats/reduces vascular calcification by mitigating the biogenesis of calcifying EVs because EGFR inhibition reduces the release of pro-calcific CAV1-positive EVs.

In one embodiment, the vascular calcification is cardiovascular calcification. In specific embodiments, the vascular calcification is medial vascular calcification or intimal atherosclerotic calcification.

In one embodiment, the subject is a human having been diagnosed with CKD, diabetes, hyperparathyroidism, hyperphosphatemia, a vitamin D disorder, a vitamin K disorder, osteoporosis, Kawasaki disease, arterial calcification due to deficiency of CD73 (ACDC), idiopathic basal ganglia calcification (IBGC), pseudoxanthoma elasticum (PXE), rheumatoid arthritis, Singleton-Merten syndrome, β-thalassemia, atherosclerosis, hyperlipidemia, hypertension, amputation, congenital bicuspid valve, and/or rheumatic heart disease.

In one embodiment, the subject invention provides a method for preventing or reducing mineral nucleation and deposition in vascular wall, e.g., cardiovascular wall, the method comprising administering, to a subject in need of such prevention or reduction, a pharmaceutical composition comprising one or more EGFR inhibitors. In preferred embodiments, the administration is local, oral, transdermal, or parenteral administration. In a specific embodiment, the subject is a human having been diagnosed with CKD or atherosclerosis.

In one embodiment, the subject invention also provides a method for preventing or reducing the formation of calcifying EVs in SMCs, the method comprising contacting SMCs with a pharmaceutical composition comprising one or more EGFR inhibitors. In a preferred embodiment, SMCs are obtained from a subject suffering from a disease associated with vascular calcification, e.g., CKD and atherosclerosis.

In one embodiment, the subject invention also provides a method for preventing or reducing the release of calcifying EVs from SMCs, the method comprising contacting SMCs with a pharmaceutical composition comprising one or more EGFR inhibitors. In a preferred embodiment, SMCs are obtained from a subject suffering from a disease associated with vascular calcification, e.g., CKD and atherosclerosis.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 1A-1K show that EGFR inhibition prevents vascular calcification in vivo and in vitro. (A) Visualization of vascular calcification using calcium tracer OsteoSense; (B) Quantification of the OsteoSense to correlate with vascular calcification burden; (C) Serum EGFR level collected from mouse groups; (D) Serum TNAP activity collected from mouse groups; (E and F) Gene expression of renal fibrotic markers, Tgfb1 and Colla1; (G) H&E staining of mouse kidney tissues (20×, scale bar 0.5 mm); (H) In vitro calcification visualization using Alizarin Red S staining and quantification; (I and J) Gene expression of osteogenic markers, RUNX2 and ALPL in VSMCs following 14 days of treatment; (K) Extracellular matrix collagen accumulation in VSMC cultures. *P<0.05, P≤0.01, *P≤0.001, and ****P≤0.0001, ANOVA with Tukey's post-hoc test.

FIGS. 2A-2K show that EGFR inhibition modulates CAV1 trafficking in VSMCs. Intracellular level of: (A) CAV1, (B) EGFR, and (C) TNAP activity in VSMCs after 14 days of culture; (D) Confocal micrographs of CAV1 distribution in VSMCs following 14 days of treatment (1200×, scale bar: 0.5 μm); Cytosolic level of: (E) CAV1, and (F) TNAP protein following 14 days of treatment; (G) CAV1 level on EVs isolated from VSMC cultures after 14, 21, and 28 days; (H) TNAP activity of the EVs isolated from VSMC cultures after 14, 21, and 28 days; EV level of: (I) EGFR, (J) Annexin V, and (K) CD63 liberated from VSMCs on day 28 of treatment. *P<0.05, P≤0.01, *P≤0.001, and ****P≤0.0001, ANOVA with Tukey's post-hoc test.

FIGS. 3A-3H show that EGFR inhibition redistributes CAV1 and TNAP in vivo. (A) Immunofluorescence staining of CAV1 and (B) cytosolic level of CAV1 in aortic tissue; (C) Immunofluorescence staining of TNAP protein and (D) cytosolic level of TNAP protein in aortic tissue; (E) Immunofluorescence staining of EGFR and (F) cytosolic level of EGFR in aortic tissue; EV Level of (G) CAV1 on EVs and (H) TNAP activity isolated from the mouse aortas. (scale bar for 10× and 100×, 200 and 20 respectively). *P<0.05, P≤0.01, *P≤0.001, and ****P≤0.0001, ANOVA with Tukey's post-hoc test.

FIGS. 4A-4H show that EGFR inhibition does not prevent osteoblast in vitro calcification. (A, B, and C) Gene expression of common osteogenic markers, RUNX2, ALPL, and BGLAP in osteoblasts following 7 days of treatment; (D) Osteoblast intracellular TNAP activity following 7 days of treatment; (E) Alizarin Red S staining and quantification of osteoblast cultures after 21 days; (F) Osteoblast intracellular CAV1 following 7 days of treatment; (G) CAV1 level on matrix vesicles liberated from osteoblasts on days 7, 14, and 21 of culture; (H) TNAP activity of matrix vesicles isolated from osteoblast cultures on days 7, 14, and 21. *P<0.05, P≤0.01, *P≤0.001, and ****P≤0.0001, ANOVA with Tukey's post-hoc test.

FIGS. 5A-5I show that EGFR inhibition does not have deleterious effects on physiological bone mineralization. 3D reconstructions of (A) femoral head, (B) cancellous bone, and (C) cortical bone resected from mouse groups (scale bar: 0.5 mm); Bone thickness at: (D) Cortical, (E) Metaphyseal trabecular, and (F) Epiphyseal trabecular regions; Bone volume fraction (%) at: (G) Cortical, (H) Metaphyseal trabecular, and (I) Epiphyseal trabecular regions. *P<0.05, P≤0.01, *P≤0.001, and ****P≤0.0001, ANOVA with Tukey's post-hoc test.

BRIEF DESCRIPTION OF SEQUENCES

Figure 1A:
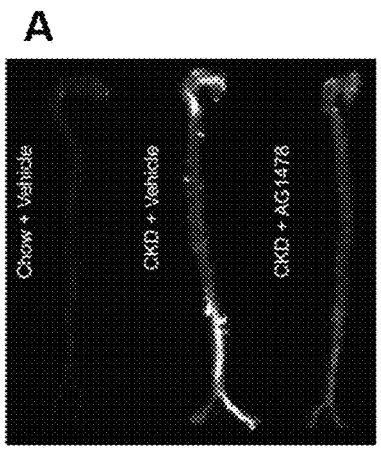

SEQ ID NO: 1 is the sequence of a forward primer for GAPDH contemplated for use according to the subject invention.

SEQ ID NO: 2 is the sequence of a reverse primer for GAPDH contemplated for use according to the subject invention.

SEQ ID NO: 3 is the sequence of a forward primer for RUNX2 contemplated for use according to the subject invention.

SEQ ID NO: 4 is the sequence of a reverse primer for RUNX2 contemplated for use according to the subject invention.

SEQ ID NO: 5 is the sequence of a forward primer for ALPL contemplated for use according to the subject invention.

SEQ ID NO: 6 is the sequence of a reverse primer for ALPL contemplated for use according to the subject invention.

SEQ ID NO: 7 is the sequence of a forward primer for Osteocalcin contemplated for use according to the subject invention.

SEQ ID NO: 8 is the sequence of a reverse primer for Osteocalcin contemplated for use according to the subject invention.

SEQ ID NO: 9 is the sequence of a forward primer for Gapdh contemplated for use according to the subject invention.

SEQ ID NO: 10 is the sequence of a reverse primer for Gapdh contemplated for use according to the subject invention.

SEQ ID NO: 11 is the sequence of a forward primer for Col1a1 contemplated for use according to the subject invention.

SEQ ID NO: 12 is the sequence of a reverse primer for Col1a1 contemplated for use according to the subject invention.

SEQ ID NO: 13 is the sequence of a forward primer for Tgfb1 contemplated for use according to the subject invention.

SEQ ID NO: 14 is the sequence of a reverse primer for Tgfb1 contemplated for use according to the subject invention.

DETAILED DESCRIPTION

The subject invention provides compounds, compositions and methods for treating, preventing and/or ameliorating excess or inappropriate vascular calcification, for example, medial vascular calcification or intimal atherosclerotic calcification, in a subject. The subject invention also provides compounds, compositions and methods for treating or preventing a disease associated with vascular calcification in a subject.

In one embodiment, the methods of the subject invention employ epidermal growth factor receptor (EGFR)-based strategies for treating, preventing and/or ameliorating vascular calcification and diseases associated with vascular calcification. The compounds and compositions of the subject invention affect and control the mechanism by which EVs in SMCs obtain their mineralizing properties for vascular calcification.

In one embodiment, the methods of the subject invention are for treating, preventing and/or ameliorating cardiovascular calcification. In another embodiment, the method is for treating, preventing and/or ameliorating Mönckeberg's arteriosclerosis, calcific atherosclerosis, calcific medial vasculopathy, elastocalcinosis, aalcific aortic valvular stenosis, portal vein calcification and/or calcific uremic arteriolopathy (CUA).

In one embodiment, the subject is suffering from chronic kidney disease (CKD), diabetes, ageing, hyperparathyroidism, hyperphosphatemia, a vitamin D disorder, a vitamin K disorder, osteoporosis, Kawasaki disease, arterial calcification due to deficiency of CD73 (ACDC), generalized arterial calcification of infancy (GACI), idiopathic basal ganglia calcification (IBGC), pseudoxanthoma elasticum (PXE), rheumatoid arthritis, Singleton-Merten syndrome and/or β-thalassemia. Optionally, vascular calcification is associated with, for example, atherosclerosis, hyperlipidemia; hypertension; T2DM; ESRD; amputation; Marfan's Syndrome; congenital bicuspid valve; rheumatic heart disease; and liver disease.

EGFR inhibitors include, for example, monoclonal antibodies (e.g., cetuximab, panitumumab, and matuzumab) that target the extracellular ligand-binding domain, and small-molecule tyrosine kinase inhibitors (e.g., vandetanib, osimertinib, gefitinib, erlotinib, lapatinib, and afatinib) that target intracellular domain.

In one embodiment, the inhibitor of EGFR can be, for example, necitumumab; saracatinib; canertinib; dacomitinib; vandetanib; neratinib; erlotinib; gefitinib; afatinib; osimertinib; lapatinib; AG1478; AG490; CP724714; WZ4002; sapitinib; CUDC-101; PD153035; pelitinib; AEE788; AC480; OSI-420; WZ3146; Allitinib; Rociletinib; Varlitinib; Icotinib; TAK-285; WHI-P154; Daphnetin; PD168393; CNX-2006; Tyrphostin 9; AG-18; Epertinib; BI-4020; Tyrphostin AG-528; SU5214; RG 13022; TQB3804; TAS6417; Pyrotinib; PD153035; AG 494; AG 555; Theliatinib; Avitinib; Lazertinib; Lifirafenib; Nazartinib; Brigatinib; Tucatinib; AZD3759; CL-387785; Poziotinib; AZ5104; and Mobocertinib.

Preferably, the inhibitor of EGFR is AG1478.

In one embodiment, the subject invention provides compositions comprising one or more EGFR inhibitors according to the subject invention and a pharmaceutically acceptable carrier.

In some embodiments, the one or more EGFR inhibitors are selected from necitumumab; saracatinib; canertinib; dacomitinib; vandetanib; neratinib; erlotinib; gefitinib; afatinib; osimertinib; lapatinib; AG1478; AG490; CP724714; WZ4002; sapitinib; CUDC-101; PD153035; pelitinib; AEE788; AC480; OSI-420; WZ3146; Allitinib; Rociletinib; Varlitinib; Icotinib; TAK-285; WHI-P154; Daphnetin; PD168393; CNX-2006; Tyrphostin 9; AG-18; Epertinib; BI-4020; Tyrphostin AG-528; SU5214; RG 13022; TQB3804; TAS6417; Pyrotinib; PD153035; AG 494; AG 555; Theliatinib; Avitinib; Lazertinib; Lifirafenib; Nazartinib; Brigatinib; Tucatinib; AZD3759; CL-387785; Poziotinib; AZ5104; cetuximab; panitumumab; matuzumab and Mobocertinib.

In one embodiment, the compounds may be in a pharmaceutically acceptable salt form or a form of free base. Examples of pharmaceutically acceptable salts include, without limitation, the nontoxic inorganic and organic acid addition salts such as acetate, aconate, ascorbate, benzenesulfonate, benzoate, cinnamate, citrate, embonate, enantate, formate, fumarate, glutamate, glycolate, hydrochloride, hydrobromide, lactate, maleate, alonate, mandelate, methanesulfonate, naphthalene-2-sulphonate, nitrate, perchlorate, phosphate, phthalate, salicylate, sorbate, stearate, succinate, sulphate, tartrate, toluene-p-sulphonate, and the like.

In one embodiment, the composition according to the subject invention also comprises a pharmaceutically acceptable carrier. "Pharmaceutically acceptable carrier" refers to a diluent, adjuvant or excipient with which the one or more active agents disclosed herein can be formulated. Typically, a "pharmaceutically acceptable carrier" is a substance that is non-toxic, biologically tolerable, and otherwise biologically suitable for administration to a subject, such as an inert substance, added to a pharmacological composition or otherwise used as a diluent, adjuvant or excipient to facilitate administration of the composition disclosed herein and that is compatible therewith.

Examples of carriers suitable for use in the pharmaceutical compositions are known in the art and such embodiments are within the purview of the invention. The pharmaceutically acceptable carriers and excipients, include, but not limited to, aqueous vehicles, water-miscible vehicles, non-aqueous vehicles, stabilizers, solubility enhancers, isotonic agents, buffering agents, suspending and dispersing agents, wetting or emulsifying agents, complexing agents, sequestering or chelating agents, cryoprotectants, lyoprotectants, thickening agents, pH adjusting agents, and inert gases. Other suitable excipients or carriers include, but are not limited to, dextran, glucose, maltose, sorbitol, xylitol, fructose, sucrose, and trehalose.

The pharmaceutical composition is used for convenient and effective administration in effective amounts with a suitable pharmaceutically acceptable carrier in an acceptable dosage unit. In the case of compositions containing supplementary active ingredients, the dosages may be determined by reference to the usual dose and manner of administration of the said ingredients.

In one embodiment, the subject invention provides compounds and compositions comprising such compounds for treating, preventing and/or ameliorating excess or inappropriate vascular calcification, for example, medial vascular calcification or intimal atherosclerotic calcification.

In one embodiment, the compositions of the subject invention can be used for preventing or reducing the formation of calcifying EVs and caveolae trafficking in vascular SMCs.

In one embodiment, the compositions of the subject invention can be used for reducing the risk of developing vascular calcification-associated diseases, e.g., coronary artery disease, in a subject (e.g., patients with diabetes, myocardial infarctions, chronic kidney disease, and/or metabolic syndrome).

In one embodiment, the compositions can be used for reducing the mineralizing properties of EVs in vascular SMCs, and for preventing or reducing mineral deposition in vascular wall.

In one embodiment, aqueous suspensions contain one or more EGFR inhibitors in admixture with excipients suitable for the manufacture of aqueous suspensions. Such excipients include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending one or more EGFR inhibitors in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. Sweetening agents can be added to provide a palatable oral preparation. These formulations can be preserved by the addition of an antioxidant such as ascorbic acid.

The pharmaceutical formulations of the subject invention can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening and flavoring agents. Syrups and elixirs can be formulated with sweetening agents, such as glycerol, sorbitol or sucrose. Such formulations can also contain a demulcent, a preservative, a flavoring or a coloring agent.

In one embodiment, the pharmaceutical composition comprising one or more EGFR inhibitors together with a conventional adjuvant, carrier, or diluent, may thus be placed into the form of solids including tablets, filled capsules, powder and pellet forms, and liquids such as aqueous or non-aqueous solutions, suspensions, emulsions, elixirs, and capsules filled with the same.

In a further embodiment, the composition is in the powder form. The pharmaceutically accepted carrier is a finely divided solid, which is in a mixture with the finely divided active compounds. In another embodiment, the composition is in the tablet form. The active component is mixed with the pharmaceutically accepted carrier having the necessary binding capacity in suitable proportions and compacted in desired shape and size. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

In a further embodiment, the composition is in other solid forms including capsules, pills, cachets, and lozenges, which are suitable for oral administration.

In one embodiment, dispersible powders and granules suitable for preparation of an aqueous suspension by the addition of water can be formulated from EGFR inhibitors in admixture with a dispersing, suspending and/or wetting agent, and one or more preservatives. Suitable dispersing or wetting agents and suspending agents are exemplified by those disclosed above.

In one embodiment, the composition is formulated in accordance with routine procedures as a pharmaceutical composition adapted for local administration to humans. Typically, compositions for local administration are solutions in a sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The pharmaceutical compositions may be formulated in any forms that are suitable for parenteral administration, including solutions, suspensions, emulsions, micelles, liposomes, microspheres, nanosystems, semi-solid, and solid forms suitable for solutions or suspensions in liquid prior to injection.

The formulations containing one or more EGFR inhibitors can be formulated for administration in any conventionally acceptable way including, but not limited to subcutaneously, intramuscularly, intravenously, sublingually, topically, orally and via inhalation.

In one embodiment, the subject invention provides a method for treating, preventing and/or ameliorating vascular calcification, for example, medial vascular calcification or intimal atherosclerotic calcification, via the inhibition of EGFR, the method comprising administering to a subject in need of such treatment, prevention or amelioration, a therapeutically effective amount of one or more EGFR inhibitors or a pharmaceutically acceptable salt or solvate thereof. In one embodiment, the subject has been diagnosed with medial vascular calcification or intimal atherosclerotic calcification.

In one embodiment, the method for treating, preventing and/or ameliorating vascular calcification further comprises administering to the subject a therapeutically effective amount of one or more EGFR inhibitors, or a pharmaceutically acceptable salt or solvate thereof.

In one embodiment, the subject invention provides a method for treating, preventing and/or ameliorating vascular calcification, e.g., medial vascular calcification or intimal atherosclerotic calcification, the method comprising administering to a subject in need of such treatment, prevention and/or amelioration, a therapeutically effective amount of a pharmaceutical composition/formulation of the subject invention, preferably, the pharmaceutical composition/formulation comprising one or more EGFR inhibitors and a pharmaceutically acceptable carrier.

"Therapeutically effective" refers to the amount of pharmaceutically active compound/molecule according to the subject invention that will result in a measurable desired medical or clinical benefit to a patient, as compared to the patient's baseline status or to the status of an untreated or placebo-treated (e.g., not treated with the compound/molecule) subject.

The term "subject" or "patient," as used herein, describes an organism, including mammals such as primates. Mammalian species that can benefit from the disclosed methods of treatment include, but are not limited to, apes, chimpanzees, orangutans, humans, and monkeys; domesticated animals such as dogs, cats; live stocks such as horses, cattle, pigs, sheep, goats, and chickens; and other animals such as mice, rats, guinea pigs, and hamsters.

In one embodiment, the subject has been diagnosed with CKD, diabetes, ageing, hyperparathyroidism, hyperphosphatemia, a vitamin D disorder, a vitamin K disorder, osteoporosis, Kawasaki disease, arterial calcification due to deficiency of CD73 (ACDC), generalized arterial calcification of infancy (GACI), idiopathic basal ganglia calcification (IBGC), pseudoxanthoma elasticum (PXE), rheumatoid arthritis, Singleton-Merten syndrome, J3-thalassemia, atherosclerosis, hyperlipidemia, hypertension, T2DM, ESRD, amputation, Marfan's Syndrome, congenital bicuspid valve, and/or rheumatic heart disease.

In one embodiment, the subject has not been diagnosed with, treated, or undergone a treatment simultaneously for inflammatory, autoimmune diseases, cancer, or metabolic disorders.

In one embodiment, images of a patient's vascular system can be obtained using virtual-histology intravascular ultrasound (VH-IVUS), and patients exhibiting early calcification can be identified therefrom. In one embodiment, a patient suffering from atherosclerotic calcification can be identified using a computed tomography (CT) scan. The CT scan can be used to calculate an Agatston score, a pseudo-continuous variable derived from plaque densities and their areas in all coronary arteries, for a patient. A patient with an Agatston score of 0 would have no coronary artery calcification. Preferably, the method of the subject invention is for use in treating atherosclerotic calcification in a patient with an Agatston score of at least 10, at least 20, at least 40, at least 60 or at least 80.

The terms "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treatment" also refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being.

The term "prevention" or any grammatical variation thereof (e.g., prevent, preventing, etc.), as used herein, includes but is not limited to, at least the reduction of likelihood of the risk of (or susceptibility to) acquiring a disease or disorder (e.g., causing at least one of the clinical symptoms of the disease not to develop in a patient that may be exposed to or predisposed to the disease but does not yet experience or display symptoms of the disease). The term "prevention" may refer to avoiding, delaying, forestalling, or minimizing one or more unwanted features associated with a disease or disorder, and/or completely or almost completely preventing the development of a disease or disorder and its symptoms altogether. Prevention can further include, but does not require, absolute or complete prevention, meaning the disease or disorder may still develop at a later time and/or with a lesser severity than it would without preventative measures. Prevention can include reducing the severity of the onset of a disease or disorder, and/or inhibiting the progression thereof.

In one embodiment, the subject invention provides a method for treating or preventing a disease associated with vascular calcification, the method comprising administering to a subject in need of such treatment or prevention a therapeutically effective amount of one or more EGFR inhibitors.

In one embodiment, the subject invention provides a method for treating or preventing a disease associated with vascular calcification, the method comprising administering to a subject in need of such treatment or prevention a therapeutically effective amount of a pharmaceutical composition/formulation of the subject invention.

The diseases associated with vascular calcification include, but are not limited to CKD, diabetes, ageing, hyperparathyroidism, hyperphosphatemia, a vitamin D disorder, a vitamin K disorder, osteoporosis, Kawasaki disease, ACDC, GACI, IBGC, PXE, rheumatoid arthritis, Singleton-Merten syndrome, β-thalassemia, atherosclerosis, hyperlipidemia, hypertension, T2DM, ESRD, amputation, Marfan's Syndrome, congenital bicuspid valve, myocardial infarctions, metabolic syndrome and rheumatic heart disease.

In one embodiment, the methods of the subject invention are for treating, preventing and/or ameliorating cardiovascular calcification via the inhibition of EGFR, the method comprising administering to a subject in need a therapeutically effective amount of the composition of the subject invention.

In one embodiment, the method is for treating, preventing and/or ameliorating Mönckeberg's arteriosclerosis, calcific atherosclerosis, calcific medial vasculopathy, elastocalcinosis, aalcific aortic valvular stenosis, portal vein calcification or calcific uremic arteriolopathy (CUA), the method comprising administering to a subject in need a therapeutically effective amount of one or more EGFR inhibitors, or a pharmaceutical composition/formulation of the subject invention. In preferred embodiments, the subject has been diagnosed with one or more of these conditions.

In one embodiment, the method of treating, preventing and/or ameliorating medial vascular calcification or intimal atherosclerotic calcification comprises administering to a subject in need of such treatment, prevention or amelioration, a therapeutically effective amount of the pharmaceutical composition/formulation of the subject invention.

In one embodiment, the subject invention also provides a method for preventing or reducing the formation of calcifying EVs and caveolae trafficking in vascular SMCs of a subject, the method comprising administering to the subject a therapeutically effective amount of one or more EGFR inhibitors, or a pharmaceutical composition/formulation of the subject invention. In a preferred embodiment, the subject has been diagnosed with CKD or arteriosclerosis.

In one embodiment, the subject invention provides a method for preventing or reducing the formation of calcifying EVs and caveolae trafficking in vascular SMCs, the method comprising contacting vascular SMCs with a therapeutically effective amount of one or more EGFR inhibitors, or a pharmaceutical composition/formulation of the subject invention, wherein vascular SMCs are obtained from a subject suffering from a disease associated with vascular calcification. In a preferred embodiment, the subject has been diagnosed with CKD or arteriosclerosis.

In one embodiment, the subject invention also provides a method for treating or reducing the risk of developing coronary artery disease, in particular, in patients with diabetes, myocardial infarctions, CKD, and metabolic syndrome, the method comprising administering to a subject in need of such prevention or reduction a therapeutically effective amount of one or more EGFR inhibitors, or a pharmaceutical composition/formulation of the subject invention. Preferably, the subject has been diagnosed with one of these conditions.

In one embodiment, the subject invention provides a method for reducing the mineralizing properties of EVs in a subject, the method comprising administering to the subject a therapeutically effective amount of one or more EGFR inhibitors, or a pharmaceutical composition/formulation of the subject invention.

In one embodiment, the subject invention provides a method for reducing the mineralizing properties of EVs in vascular SMCs, the method comprising contacting vascular SMCs with one or more EGFR inhibitors, or a pharmaceutical composition/formulation of the subject invention. In a specific embodiment, EVs have an average diameter of about 90 nm to 110 nm, or about 100 nm.

In one embodiment, the subject invention provides a method for preventing or reducing mineral nucleation and deposition in vascular wall of a subject, the method comprising administering to the subject in need a therapeutically effective amount of one or more EGFR inhibitors, or a pharmaceutical composition/formulation of the subject invention.

In one embodiment, the subject invention provides a method for preventing or reducing mineralization in the vascular system of a subject, the method comprising administering to the subject a therapeutically effective amount of one or more EGFR inhibitors, or a pharmaceutical composition/formulation of the subject invention.

In one embodiment, the subject invention provides a method for treating, preventing and reducing calcification of vascular SMCs, the method comprising administering to the subject in need a therapeutically effective amount of one or more EGFR inhibitors, or a pharmaceutical composition/formulation of the subject invention.

In specific embodiments, the subject invention provides methods for treating intimal atherosclerotic and/or medial CKD calcification in a subject diagnosed therewith, the method comprising administering to the subject in need a therapeutically effective amount of one or more EGFR inhibitors, or a pharmaceutical composition/formulation of the subject invention.

In some embodiments, the one or more EGFR inhibitors for use in the methods according to the subject invention are selected from necitumumab; saracatinib; canertinib; dacomitinib; vandetanib; neratinib; erlotinib; gefitinib; afatinib; osimertinib; lapatinib; AG1478; AG490; CP724714; WZ4002; sapitinib; CUDC-101; PD153035; pelitinib; AEE788; AC480; OSI-420; WZ3146; Allitinib; Rociletinib; Varlitinib; Icotinib; TAK-285; WHI-P154; Daphnetin; PD168393; CNX-2006; Tyrphostin 9; AG-18; Epertinib; BI-4020; Tyrphostin AG-528; SU5214; RG 13022; TQB3804; TAS6417; Pyrotinib; PD153035; AG 494; AG 555; Theliatinib; Avitinib; Lazertinib; Lifirafenib; Nazartinib; Brigatinib; Tucatinib; AZD3759; CL-387785; Poziotinib; AZ5104; and Mobocertinib. Preferably, the inhibitor of EGFR is AG1478.

In certain embodiments, EGFR inhibitors contact vascular SMCs at a concentration ranging from about 1 nM to about 500 µM, from about 10 nM to about 400 µM, from about 20 nM to about 300 µM, from about 50 nM to about 200 µM, from about 100 nM to about 150 µM, from about 200 nM to about 100 µM, from about 500 nM to about 100 µM, from about 500 nM to about 50 µM, from about 1 µM to about 25 or from about 1 µM to about 10 µM.

The compositions of the present invention can be administered to the subject being treated by standard routes, including the local, oral, ophthalmic, nasal, topical, transdermal, intra-articular, parenteral (e.g., intravenous, intraarterial, intraperitoneal, intrathecal, intraventricular, intradermal, intracavity, subcutaneous or intramuscular), intracranial, intracerebral, intraspinal, intrauterine, or rectal route. Depending on the condition being treated, one route may be preferred over others, which can be determined by those skilled in the art. Preferably, the composition is administered by injection (e.g., IV injection), gradual infusion over time or implantation.

Depending on the route of administration, the pharmaceutical composition can be associated with a material to protect the pharmaceutical composition from the action of enzymes, acids, and other natural conditions that may inactivate the pharmaceutical composition. Dispersions can also be prepared in glycerol, liquid polyethylene glycols, and mixtures thereof, and in oils. Under ordinary conditions of storage and use, these preparations may contain a preservative to prevent the growth of microorganisms.

Administration can be carried out using therapeutically effective amounts of the agents described herein for periods of time effective according to the subject invention. The effective amount may be determined by one of ordinary skill in the art and includes exemplary dosage amounts for a subject of from about 0.005 to about 500 mg/kg of body weight of active compound per day, which may be administered in a single dose or in the form of individual divided doses, such as from 1 to 4 times per day.

Alternatively, the dosage amount may be from about 0.01 to about 450 mg/kg of body weight of active compound per day, from about 0.05 to about 400 mg/kg of body weight of active compound per day, from about 0.1 to about 300 mg/kg of body weight of active compound per day, from about 0.1 to about 250 mg/kg of body weight of active compound per day, from about 0.2 to about 200 mg/kg of body weight of active compound per day, from about 0.5 to about 150 mg/kg of body weight of active compound per day, from about 0.5 to 100 mg/kg of body weight of active compound per day, from about 0.5 to about 75 mg/kg of body weight of active compound per day, from about 0.5 to about 50 mg/kg of body weight of active compound per day, from about 0.5 to about 25 mg/kg of body weight of active compound per day, from about 1 to about 20 mg/kg of body weight of active compound per day, from about 1 to about 15 mg/kg of body weight of active compound per day, from about 1 to about 10 mg/kg of body weight of active compound per day.

In specific embodiments, the dosage amount may be about 500 mg/kg of body weight of active compound per day, about 400 mg/kg of body weight of active compound per day, about 300 mg/kg of body weight of active compound per day, about 200 mg/kg of body weight of active compound per day, about 100 mg/kg of body weight of active compound per day, about 50 mg/kg of body weight of active compound per day, 20 mg/kg of body weight of active compound per day, about 10 mg/kg of body weight of active compound per day, about 5 mg/kg of body weight of active compound per day, about 1 mg/kg of body weight of active compound per day, about 0.5 mg/kg of body weight of active compound per day, or about 0.1 mg/kg of body weight of active compound per day.

In specific embodiments, the composition of the subject invention may be administered at least once a day, twice a day, or three times a day for consecutive days, e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. The composition of the subject invention may also be administered for weeks, months or years.

As used herein, the reduction or delay in onset, incidence or severity according to the method of the subject invention can be about a 5%, 10%, 15%, 20%, 25%, 30%, 40%, 50%, 60%, 70%, 80%, 90%, 100%%, or any amount of reduction in between.

In one embodiment, the method according to the subject invention further comprises a step of evaluating the treatment or reduction in response to one or more EGFR inhibitors or the pharmaceutical composition of the subject invention.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably.

The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

EXAMPLES

Materials and Methods

Chronic Kidney Disease and Vascular Calcification Mouse Model

The in vivo study was approved by the Institutional Animal Care and Use Committee (IACUC) at Florida International University under protocol AN20-006 and conformed to current NIH guidelines. 8-week-old wild type C57BL/6J mice (n=38, 19 per biological sex) were fed an adenine-supplemented diet (0.2%, TestDiet, Richmond, Ind.) for 6 weeks to induce severe kidney injury. The mice then received a diet containing 1.8% phosphate (TestDiet, Richmond, Ind.) and 0.2% adenine for an additional two weeks to induce medial calcinosis.

Along with this calcifying diet, a group of mice (n=19) received daily tyrphostin AG1478 (10 mg/kg mouse, Millipore Sigma, T4182) via oral gavage. The remaining mice (n=19) received vehicle treatment (1% w/v, carboxymethylcellulose sodium salt, Sigma, C5678). For non-diseased controls, a third group of mice (n=12, 6 per biological sex) were fed a regular chow diet and received the vehicle for the final two weeks. During the oral gavage, animals were partially anesthetized using isoflurane (1%, Patterson Veterinary, 07-893-1389, in 2 L.min$^{-1}$ oxygen flow). All animals received a tail vein injection with the calcium tracer OsteoSense 680EX (80 nmol/kg mouse, PerkinElmer, NEV10020EX) 48 hours prior to euthanization. At study endpoint, mice were anesthetized with isoflurane (1%, in 2 L.min$^{-1}$ oxygen flow) followed by retro-orbital bleeding for blood collection. Mice were then immediately euthanized by laceration of the diaphragm before tissue collection. After resection, the aortas were imaged using a near-infrared scanner (LI-COR Odyssey) to visualize the vascular calcification burden. A custom MATLAB script quantified the total area of the calcium tracer, which was normalized to the total scanned aorta area.

Immediately after scanning, the tissue was incubated in a digestive solution of sucrose (0.25 M, Sigma, S7903), NaCl (0.12 M, Fisher Chemical, BP358), KCl (0.01 M, Fisher Chemical, P217), Tris hydrochloride (0.02 M, Fisher Chemical, BP153), and collagenase (600 U/mL, Worthington Biochemical, LS004174) for 2 hours at 37° C. The solution was then centrifuged at 1,000×g for 15 min to remove cell debris and at 33,000×g for 30 min to remove microvesicles. Finally, the supernatants were ultracentrifuged (Beckman Coulter, Optima MAX-TL) at 100,000×g for 1 hour to isolate the EVs of interest. The pellet was suspended in RIPA lysis and extraction buffer (G Biosciences, 786-489) supplemented with pierce protease inhibitor (Thermo Scientific, A32963). To yield sufficient protein concentration for analysis, EVs isolated from 2 to 3 aortas were pooled.

Osteogenic Stimulation, In vitro Calcification, and Extracellular Vesicles Isolation Primary human coronary artery vascular smooth muscle cells, (VSMCs, ATCC, PCS-100-021) were cultured using vascular smooth muscle cell media and growth kit (ATCC, PCS-100-042). VSMCs (passage 4-6) were harvested using 0.05% trypsin-EDTA solution (Caisson Labs, TRL04) and seeded with a density of 26,320 cells.cm$^{-2}$ and incubated for 72 hours at 37° C., 5% $CO_2$ with controlled humidity prior to treatment. VSMCs were treated with either control media, consisting of DMEM (HyClone, SH30022.01), 10% v/v bovine calf serum (iron-supplemented, R&D Systems, S11950), and 1% v/v penicillin-streptomycin (Gibco, 15070-063), or with an osteogenic media (OS) optimized to induce calcification. OS media were supplemented with 10 mM β-glycerophosphate (Sigma, 13408-09-8), 0.1 mM L-ascorbic acid (Sigma, 113170-55-1), and 10 nM dexamethasone (Sigma, 50-02-2).

To assess the role of EGFR inhibition, tyrphostin AG1478 (Millipore Sigma, T4182) was dissolved in vehicle (DMSO: Methanol, 1:1) and added to OS media to a final concentration of 2.5 µM. An equal volume of vehicle was added to the control and OS groups. It shown that 28 days in OS culture media led to robust calcification by VSMCs; therefore, all cultures (n=3, independent donors, male and female) were treated for 28 days and media were replaced every three days. On days 6, 13, 20, and 27 the media were replaced by an extracellular-vesicle-free (EV-free) media (ultracentrifuged for 15 hours at 100,000×g at 4° C. to remove background EVs common in the serum). After 24 hours, conditioned media were collected on days 7, 14, 21, and 28. Collected media were centrifuged at 1,000×g for 5 min to remove cell debris. EV isolation was performed using ultracentrifugation (Beckman Coulter, Optima MAX-TL) at 100,000×g for 1 hour.

Osteoblasts (from human fetus, hFOB 1.19, ATCC, CRL-11372) were cultured and grown in DMEM containing 10% v/v bovine calf serum and 1% v/v penicillin-streptomycin. Osteoblasts (passage 4-6) were harvested using 0.25% trypsin-EDTA solution (Caisson Labs, TRL01), seeded with a density of 5,200 cell.cm$^{-2}$, and incubated for 24 hours at 37° C. and 5% $CO_2$ with controlled humidity. The cells were treated in three groups of control, OS, and OS supplemented with tyrphostin AG1478 (2.5 µM) for 21 days and media changed every three days. Compared to VSMCs, more rapid mineralization were observed in osteoblasts cultured in OS with full matrix mineralization apparent after 21 days. Similar to the VSMC experiments, EV-free media were added to the cultures on days 6, 13, and 20, and collected 24 hours later on days 7, 14, and 21. Collected media were centrifuged at 1,000×g for 5 min to remove cell debris. EVs were isolated using the ultracentrifugation at 100,000×g for 1 hour.

Alizarin Red S Quantification and Quantification

At the end of experiments (28 and 21 days of treatment on VSMCs and osteoblasts, respectively), media were removed, and the cells were fixed using Formalin (10%, Fisher Chemical, SF100). To visualize in vitro calcification, Alizarin Red S stain (ARS, Ricca, 500-32) was added to the wells and incubated for 30 min at room temperature. The stain was then removed, and the cells were washed three times with milliQ water.

To quantify the in vitro calcification, ARS stain was extracted using acetic acid (1.67 M, Fisher Chemical, A38S) on a shaker. After 30 min, the supernatants were collected, briefly vortexed, heated at 85° C. for 10 min. The samples were cooled on ice for 5 min and centrifuged at 20,000×g for 15 min to remove background particles. Sample absorbance of 405 nm was measured using a multi-mode reader (BioTek, Synergy HTX).

Kidney Histological Analysis

To assess histological changes in kidneys due to renal injury, Hematoxylin and Eosin (H&E) staining was performed. The kidneys resected from the mice were fixed using formalin (10%) for three hours. Tissues were embedded using Tissue-Plus OCT (Fisher Scientific, 23-730-571). The samples were cryosectioned with a thickness of 12 µm and stained using rapid chrome H&E staining kit (Thermo Scientific, 9990001).

Quantitative Real Time Polymerase Chain Reaction

Following 7 or 14 days of treatment with control, OS, and OS plus EGFR inhibitor media, VSMCs and osteoblasts were lysed in 1 mL TRIzol solution (Invitrogen, 15596018). Total RNA was isolated according to the manufacturer's protocol. To perform the quantitative real time polymerase chain reaction (qRT-PCR), Power SYBR Green RNA-to-CT 1-Step Kit (Applied Biosystems, 4391178) was used. 50 ng isolated template RNA were added to each reaction for qRT-PCR. The results were normalized relative to Glyceraldehyde 3-phosphate dehydrogenase (GAPDH) expression level as the housekeeping control. The relative gene expression levels were calculated using comparative CT method, considering control groups as the reference.

The following human primer sequences were purchased from Integrated DNA Technologies (IDT); GAPDH Forward: CTTCGCTCTCTGCTCCTCCTGTTCG (SEQ ID NO: 1) and Reverse: ACCAGGCGCCCAATACGAC-CAAAT (SEQ ID NO: 2); RUNX2 Forward: GCTCTCTAACCACAGTCTATGC (SEQ ID NO: 3) and Reverse: AGGCTGTTTGATGCCATAGT (SEQ ID NO: 4); ALPL Forward: GGAGTATGAGAGTGACGAGAAAG (SEQ ID NO: 5) and Reverse: GAAGTGGGAGTGCTTGTATCT (SEQ ID NO: 6); Osteocalcin Forward: TCACACTCCTCGCCCTATT (SEQ ID NO: 7) and Reverse: CCTCCTGCTTGGACACAAAA (SEQ ID NO: 8).

To isolate RNA from the resected kidneys, the tissues were homogenized using a grinder (Sigma, Z529672) and lysed in 1 mL TRIzol solution. After 10 min incubation at room temperature, the samples were centrifuged at 12,000×g for 10 min at 4° C. The supernatants were collected and 200 µL of chloroform (Sigma Aldrich, C2432) were added to each sample. The samples were vortexed, incubated at room temperature for 10 min, and centrifuged for 15 min at 12,000×g, 4° C. The aqueous phase was collected from each sample and 500 µL of isopropanol was added; the samples were vortexed, incubated for 15 min at room temperature following by 15 min on ice, and centrifuged at 21,000×g for 15 min. The supernatants were discarded, and pellets were washed twice with 500 µL cold ethanol (75% v/v) and centrifuged at 21,000×g for 5 min. The isolated RNA templates were heated at 65° for 15 min, and the concentrations were measured using a spectrophotometer (NanoDrop Lite, Thermo scientific). Power SYBR Green RNA-to-CT 1-Step Kit with 100 ng isolated template RNA per reaction was used.

The following mouse primer sequences were purchased from Eurofins Scientific; Gapdh Forward: AACGACCCCTTCATTGAC (SEQ ID NO: 9) and Reverse: TCCACGACATACTCAGCAC (SEQ ID NO: 10); Col1a1 Forward: CCTCAGGGTATTGCTGGACAAC (SEQ ID NO: 11) and Reverse: ACCACTTGATCCAGAAGGACCTT (SEQ ID NO: 12); Tgfb1 Forward: TGGAGCAACATGTGGAACTC (SEQ ID NO: 13) and Reverse: CAGCAGCCGGTTACCAAG (SEQ ID NO: 14).

Alkaline Phosphatase Activity Assay

To assess the activity of intracellular tissue non-specific alkaline phosphatase (TNAP), a colorimetric assay kit (BioVision, K412) was used. VSMCs (n=3) after 14 days and osteoblasts (n=3) after 7 days, were lysed in 120 µL assay buffer. 80 µL of each sample were mixed with 50 µL of 5 mM pNPP solution and incubated for 60 min at 25° C. The colorimetric change resulting from the reaction was detected using a plate reader to measure absorbance at 405 nm. The results were normalized to the total protein for associated samples measured by a BCA protein assay (BioVision, K813).

For EV TNAP activity measurement, after ultracentrifugation at 100,000×g for 1 hour, the pellets were re-suspended in 120 µL buffer assay. The assessment was performed using the same assay protocol described for intracellular TNAP activity and the results were normalized to the total protein for each sample. For mice serum TNAP activity, the samples were diluted 1:20 and assessment was performed according to the manufacturer's protocol.

Extracellular Collagen Assessment

After 28 days of treatment, soluble collagen was extracted from the cultures using acetic acid (0.5 M) through overnight incubation at 4° C. A colorimetric assay, Sircol soluble collagen assay (Biocolor, S1000), measured the total soluble extracellular matrix (ECM) collagen in each group. Samples were prepared and assessed according to the manufacturer's protocol. Results were then normalized to the total protein measured using BCA assay.

Subcellular Fractionation for VSMCs and Aortas 8-week-old wild type C57BL/6J mice (n=20, female) received the adenine-supplemented diet for 6 weeks to induce CKD, followed by two additional weeks of the diet containing 1.8% phosphate and 0.2% adenine to induce medial calcinosis. Mice were split into two groups (10 per group). The first group received daily tyrphostin AG1478 (10 mg/kg mouse), while the other group received vehicle (1% w/v, carboxymethylcellulose sodium salt). At study endpoint, the animals were euthanized, and the aortas were resected.

A subcellular protein fractionation kit for tissue (Thermofisher, 87790) was used to isolate cellular cytosolic fraction from the resected aortas, using the manufacturer's protocol. Briefly, the tissues were minced and homogenized using a grinder. The samples were then incubated in a cytoplasmic extraction buffer for 10 min at 4° C., followed by centrifugation at 1000×g for 5 min. The supernatants yielded the cytosolic fraction. To obtain sufficient protein for analyses, two aortas were pooled per data point.

VSMCs were treated with control, OS, and OS supplemented with tyrphostin AG1478 (2.5 µM) for 14 days. At the experiment endpoint, using a subcellular protein fraction kit for cultured cells (Thermofisher, 78840), cytosolic fraction was isolated according to the manufacturer's protocol. Briefly, VSMCs were harvested using 0.25% trypsin solution and resuspended in cytoplasmic extraction buffer. After 10 min incubation at 4° C., the samples were centrifuged at 1000×g for 5 min and the supernatants were collected as cytosolic fractions. The protein concentration for aortic tissue and VSMC fractions were quantified using a BCA assay and samples were prepared for protein immunoblotting.

Gel Electrophoresis and Protein Immunoblotting

VSMCs, osteoblasts, isolated EVs (either from cells or mouse aortas), and matrix vesicles (from osteoblasts) were lysed in RIPA lysis and extraction buffer supplemented with protease inhibitor. After adding Laemmli SDS-sample buffer (1:4 v/v, Boston BioProducts, BP-110R) to each lysate, the samples were denatured at 100° C. for 10 min, loaded into 7.5-12% 1-mm SDS-PAGE gel (15 to 20 µg protein per lane), and run at 170 V. The proteins were then transferred to Trans-Blot turbo nitrocellulose membranes (BIO-RAD, 1704158) at 25 V for 7 min.

To quantify the total protein, the membranes were stained using 2% w/v Ponceau stain (Alfa Aesar, AAJ6074409) for 20 min, followed by one wash with 5% acetic acid and milliQ water for 5 min. After imaging, the intensity of each lane was measured in ImageJ for total protein normalization. Membranes were blocked with 5% w/v bovine serum albumin (HyClone, SH30574.01) in TBS-Tween (1×) for 1 hour. The membranes were incubated with primary antibodies of interest, including CAV1 (1:200, Abcam, ab2910), TNAP (1:200, Invitrogen, 702454), EGFR (1:00, EMD Millipore, 06-874), CD63 (1:200, Abeam, ab231975), GAPDH (1:100, Abcam, ab181602), and Annexin V (1:200, proteintech, 11060-1-AP) overnight at 4° C. After three washes with TBS-Tween (1×), the membranes were incubated with secondary antibody (1:1000, Li-Cor) for 1 hour, followed by three washes with TBS-Tween (1×). The protein bands were visualized with Odyssey CLx scanner (Li-Cor), and quantified using Image Studio Lite software (Li-Cor).

Immunofluorescence Staining and Imaging

VSMCs were fixed after 14 days of culture using formalin (10%) for 15 min and washed with PBS. A solution of PBS and Triton X (0.1% v/v) permeabilized the plasma membrane for 10 min at room temperature. To avoid non-specific antibody binding, the cells were incubated with a blocking buffer solution, consisting of BSA (1% w/v) and glycine (22.5 mg/mL) in PBS for 30 min at room temperature. Next, the cells were incubated for 2 hours with primary antibody against CAV1 (1:200), and washed three times with PBS. Cells were then incubated with a secondary antibody, Alexa Fluor 594 (1:500, Abeam, ab150080) for 1 hour at room temperature, following by three washes with PBS. The nuclei were stained using DAPI (0.2 mg/mL, Cayman Chemical, 14285). To visualize actin filaments, samples were incubated for 30 min with Phalloidin-iFluor 488 conjugate (1:50, Cayman Chemical, 20549) followed by three washes with PBS.

Resected aortae were fixed in formalin (10%) for 2 hours. The tissues were rinsed with PBS and embedded in OCT. The samples were cryosectioned with a thickness of 7 µm. The samples were incubated with a blocking buffer containing donkey serum (10% v/v), Triton X (0.3% v/v), BSA (1% w/v) in PBS for 1 hour at room temperature. After blocking buffer removal, a solution of donkey serum (1% v/v), Triton X (0.3% v/v), BSA (1% w/v) in PBS, with primary antibody against either CAV1(1:200), EGFR (1:100), or TNAP (1:200) was added to the samples. After an hour incubation at room temperature, the primary antibody solution was removed and the samples were washed with PBS. Secondary antibody, Alexa Fluor 594 (1:500, Invitrogen, A21207) was added to the samples and incubated for 1 hour at room temperature. After washing the samples with PBS, samples were stained with DAPI (0.2 µg/mL, Cayman Chemical, 14285) for 10 min and washed with PBS. The samples were mounted using Flouromount (Sigma Millipore, F4680). A confocal microscopy system (Eclipse Ti, Nikon) was used to image both cellular and tissue samples.

X-ray Computed tomography (X-ray CT)

Femurs were dissected from mice, wrapped in parafilm and imaged directly in a Nikon XT H 225 scanner (macro-CT, Nikon Metrology, Tring, UK). The raw transmission images were reconstructed using commercial image reconstruction software package (CT Pro 3D, Nikon Metrology, Tring, UK), which employs a filtered back-projection algorithm. The scan was performed using 80 kV beam energy, 70 µA beam current, and a power of 5.6 W. A PerkinElmer 1620 flat panel detector was used, with 200 µm pixel size. The resulting effective pixel size was 5 µm. The exposure time per projection was 0.5 s, and a total of 1601 projections were acquired, resulting in a scanning time of approximately 13 minutes per sample. Bone structural parameters, including thickness and volume fraction (the ratio of bone volume (BV) to total volume (TV)), for both cortical and trabecular regions were assessed using a plug-in module, BoneJ, in ImageJ (NIH, USA).

Statistics

Data are presented as the mean of independent replications, and error bars represent the standard error of the mean. The reported n values represent independent biological replicates. Statistical significance between groups was calculated using one-way ANOVA with Tukey's post-hoc test in GraphPad Prism 8. A p-value less than 0.05 was considered statistically significant. In case of comparison between two groups, the statistical significance was calculated using t-test with p-values less than 0.05.

Example 1—EGFR Inhibition Reduces Vascular Calcification in a CKD Mouse Model

Figure 1B:
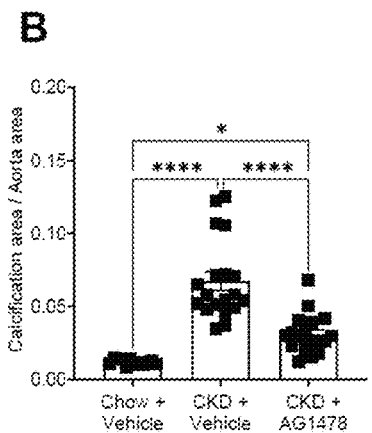
Figure 1C:
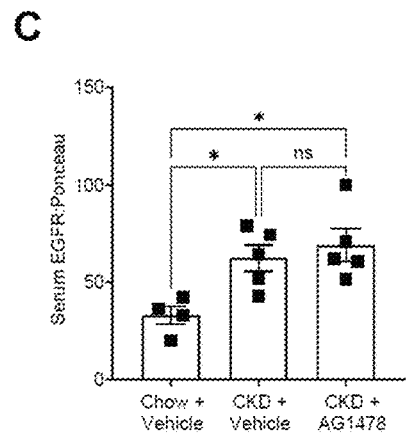

Visualization of the calcium tracer, OsteoSense, showed widespread vascular calcification in CKD mice compared to the chow-fed control group. Daily EGFR inhibitor gavage (10 mg/kg mouse) for two weeks dramatically reduced vascular calcification in CKD animals (FIG. 1A). Quantification of the OsteoSense intensity revealed a significant reduction in vascular calcification in EGFR inhibited group ($p \leq 0.001$) as shown in FIG. 1B. The level of serum EGFR was elevated in the CKD group compared to chow fed animals ($p=0.038$), with no significant difference between CKD and EGFR inhibited groups ($p=0.78$) (FIG. 1C).

Figure 1D:
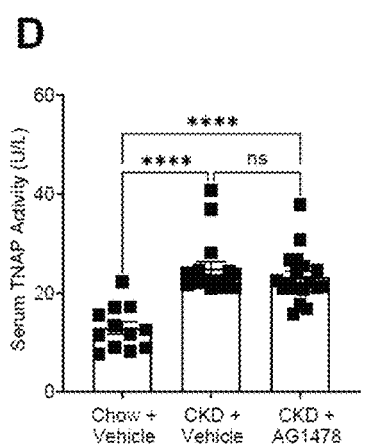
Figure 1E:
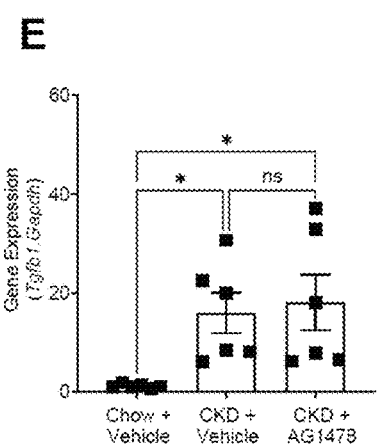
Figure 1F:
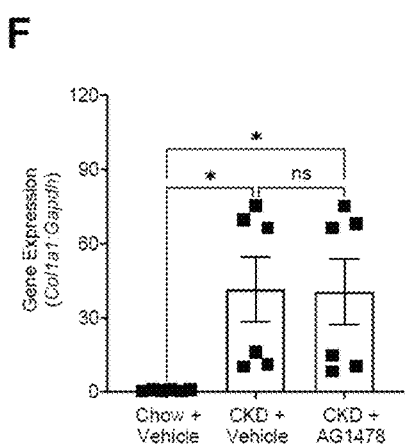

Further, serum TNAP activity (FIG. 1D) in CKD animals was significantly elevated compared to the control group ($p=0.003$). EGFR inhibition did not significantly reduce serum TNAP activity ($p=0.06$). Gene expression of common renal fibrosis markers, Tgfb1 and Colla1 (FIGS. 1E and 1F), were significantly increased in both CKD mice ($p=0.02$ and $p=0.02$ for Tgfb1 and Colla1, respectively) and CKD mice treated with EGFR inhibitor ($p=0.02$ and $p=0.03$ for Tgfb1 and Colla1, respectively) when compared to chow-fed control, with no significant differences between the CKD groups ($p=0.7$ and $p=0.6$ for Tgb1 and Colla1 respectively). Qualitative assessment of histological sections of resected kidney tissues showed enlarged tubular structures in both CKD and EGFR inhibitor treated CKD groups, compared to the chow-fed control (FIG. 1G). These results indicate that EGFR inhibition reduces vascular calcification in CKD animals independent of effects on renal injury.

Example 2—EGFR Inhibition Attenuates In Vitro Vascular Smooth Muscle Cell Calcification VSMC cultured calcified following 28 days of culture in OS media, as shown by ARS staining (FIG. 1H, representative image). Treatment of OS cultures with EGFR inhibitor abrogated in vitro calcification of VSMCs (FIG. 1H). Gene expression analysis of the common osteogenic markers RUNX2 and ALPL revealed that VSMCs cultured in both OS ($p=0.02$ and $p=0.02$ for RUNX2 and ALPL, respectively) and OS treated with EGFR inhibitor ($p=0.04$ and $p=0.03$ for RUNX2 and ALPL, respectively) acquired an osteogenic phenotype after 14 days of culture (FIGS. 1I and 1J) with no significant differences between the groups ($p=0.42$ and $p=0.1$ for RUNX2 and ALPL, respectively).

Moreover, OS media promoted the accumulation of ECM collagen in vitro, which creates a platform for calcifying EVs to initiate calcification (FIG. 1K). EGFR inhibition did not affect the ECM collagen accumulation ($p=0.10$). These data indicate that EGFR inhibition attenuates VSMC calcification without affecting VSMC phenotypic changes.

Example 3—EGFR Inhibition Alters CAV1/TNAP Intracellular Trafficking

Both OS and OS cultured VSMCs treated with EGFR inhibitor significantly increased the total level of intracellular CAV1 in VSMCs compared to the control group ($p<0.0001$) (FIG. 2A). OS media also increased intracellular EGFR in VSMCs compared to the control group ($p=0.019$, FIG. 2B). EGFR inhibition prevented the OS-induced increase in EGFR protein ($p=0.84$). Similar to the gene expression data (FIG. 1J), both OS and OS cultured VSMCs treated with EGFR inhibitor exhibited elevated intracellular TNAP activity ($p=0.03$ and $p=0.03$ for intracellular CAV1 and TNAP activity, respectively, compared to control) (FIG. 2C). Confocal micrographs of VSMCs (FIG. 2D) showed alignment of CAV1 protein along actin filaments in VSMCs cultured in OS media.

In the OS cultured VSMCs treated with EGFR inhibitor, larger clusters of CAV1 were observed between filaments.

Subcellular protein fractionation of VSMCs revealed that both cytosolic CAV1 and TNAP were elevated in EGFR inhibited cultures compared to control (p=0.02 and p=0.003, respectively) and OS groups (p=0.04 and p=0.005, respectively, FIGS. 2E and 2F).

Qualitative analysis of confocal micrographs of CAV1, EGFR, and TNAP immunofluorescence in the aorta of mice indicated elevation of all three proteins in CKD mice and CKD mice treated with EGFR inhibitor, compared to the chow-fed controls (FIGS. 3A, 3C, and 3E). Subcellular protein fractionation of aorta indicated higher cytosolic CAV1 and TNAP proteins in EGFR inhibited CKD animals compared to the CKD group (p=0.04 and p=0.0001, and p=0.018, respectively), similar to in vitro data (FIGS. 3B, 3D, and 3F).

Figure 3G:
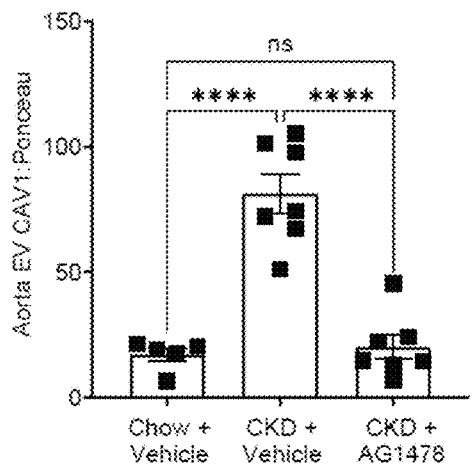
Figure 3H:
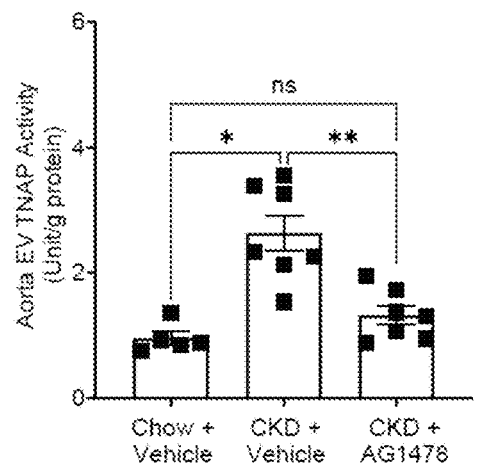

Example 4—EGFR Inhibition Reduces the Release of CAV1-Positive EVs with High TNAP Activity In Vitro and In Vivo EVs isolated from the aortas of CKD mice exhibited significantly elevated CAV1 protein and TNAP activity compared to chow-fed controls (p<0.0001 and p=0.02 for CAV1 and TNAP activity, respectively, FIGS. 3G and 3I1). The EVs isolated from the CKD mice treated with EGFR inhibitor had significantly lower CAV1 protein and TNAP activity (p<0.0001 and p=0.003 for CAV1 and TNAP activity, respectively, FIGS. 3G and 3H).

Figure 2G:
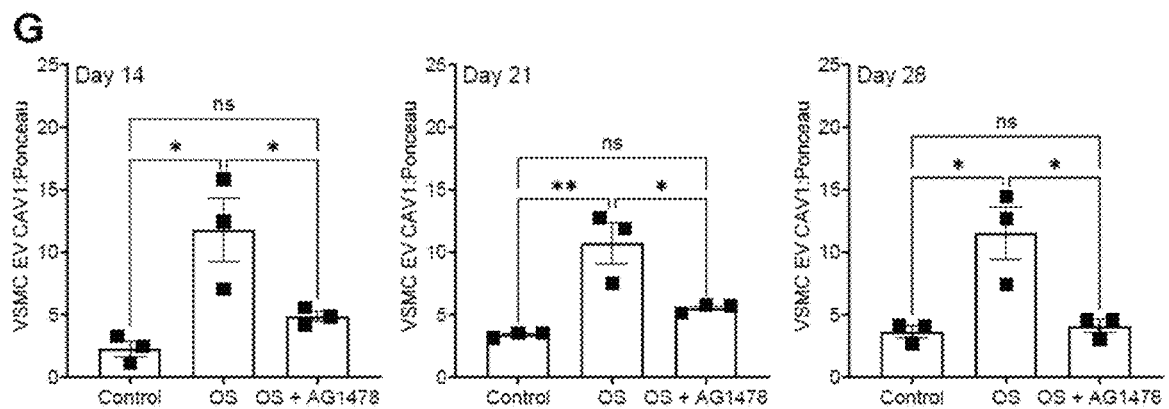
Figure 2H:
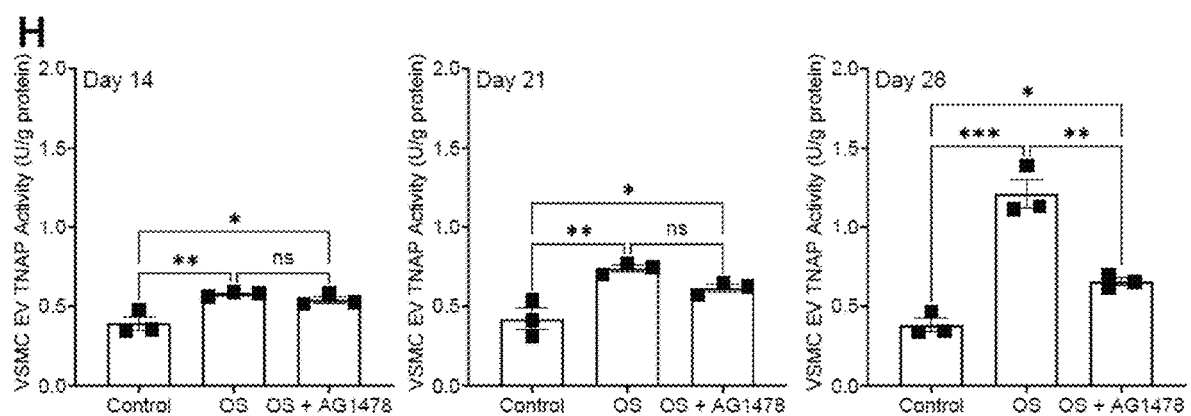

The EGFR inhibition led to similar outcomes in vitro. EVs obtained from VSMCs cultured in OS media contained significantly elevated CAV1 after 14, 21, and 28 days compared to controls (FIG. 2G). EV TNAP activity increased in OS VSMC cultures over time (FIG. 2H). EGFR inhibition reduced the release of CAV1-positive EVs by VSMCs (FIG. 2G) and EV TNAP activity (FIG. 2H).

Furthermore, EVs isolated from VSMCs cultured in OS media were enriched with Annexin V, a calcium-binding protein, and EGFR (FIGS. 2I and 2J); EGFR inhibited groups showed reduced levels of Annexin V and EGFR on the EVs. Of note, the level of CD63, a common marker of the EVs, was preserved across the in vitro groups following 28 days of culture (p=0.9 between the groups), as shown in FIG. 2K.

Figure 4A:
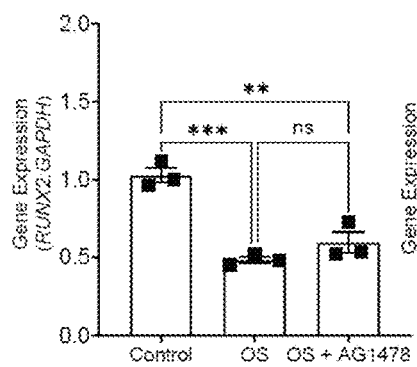
Figure 4B:
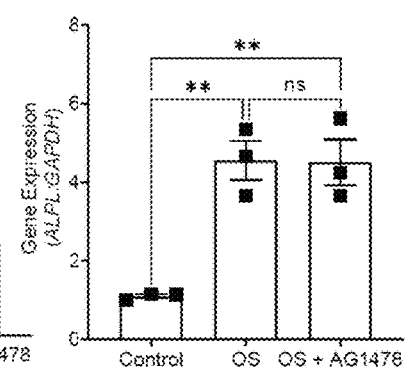
Figure 4C:
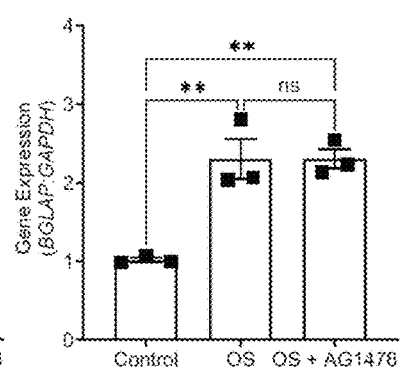
Figures 4D, 4E, 4F:
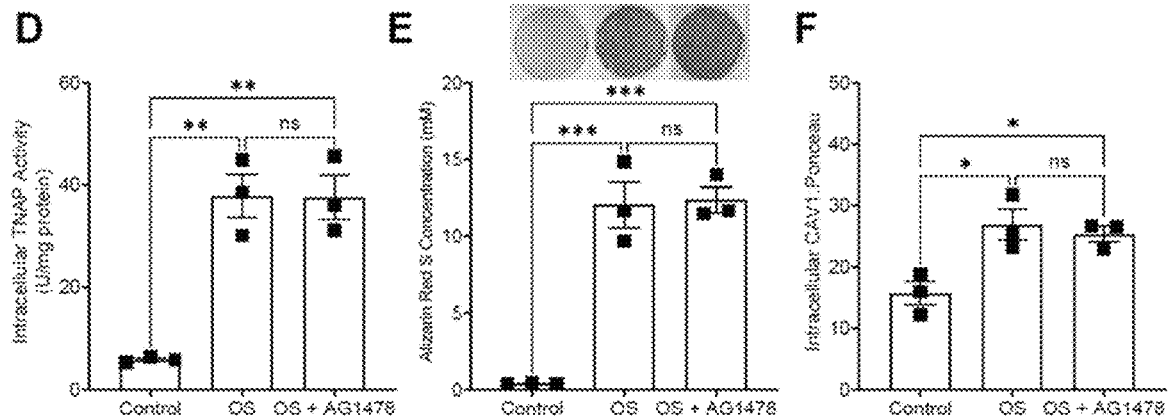

Example 5—EGFR Inhibition does not Cause Deleterious Effects on Physiological Bone Mineralization Both OS and OS cultured osteoblasts treated with EGFR inhibitor committed to osteogenic transition by downregulation of RUNX2 (FIG. 4A) and increased expression of ALPL and Osteocalcin (BGLAP), after 7 days (FIGS. 4B and 4C), with no significant differences between the groups (p=0.9 and p=0.9 for ALPL and BGLAP, respectively). Similar to ALPL expression, the osteoblasts demonstrated significantly increased intracellular TNAP activity after 7 days in both cultures (FIG. 4D). Alizarin red staining demonstrated in vitro calcification in both groups and quantification of the in vitro calcification showed no significant difference between the groups (p=0.86, FIG. 4E).

Figure 4G:
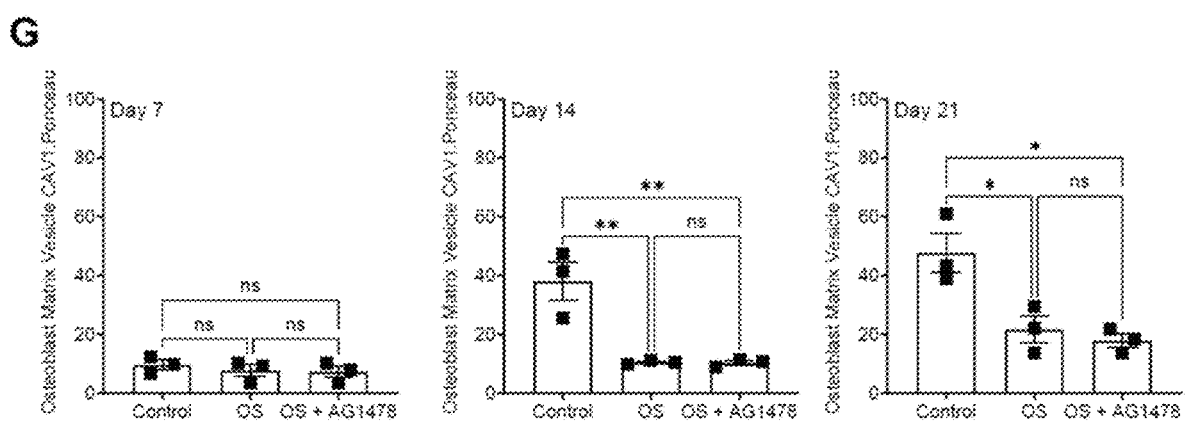

In both OS and OS cultured osteoblasts treated with EGFR inhibitor, intracellular CAV1 protein was significantly increased compared to the control group (p=0.02 and p=0.01 for the OS and OS with EGFR inhibitor groups, respectively, FIG. 4F). Matrix vesicles released by osteoblasts in both OS and OS treated with EGFR inhibitor groups had significantly increased TNAP activity; however, the EVs from these cells had lower levels of CAV1 protein compared to control on days 14 and 21 in culture (FIGS. 4G and 4I1).

Figure 5D:
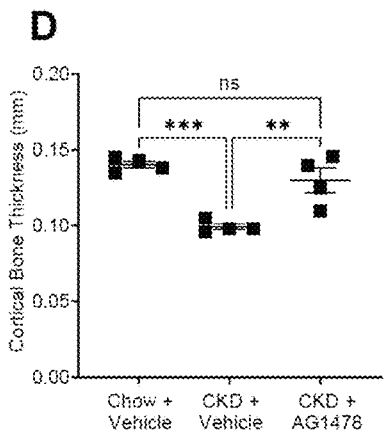
Figure 5E:
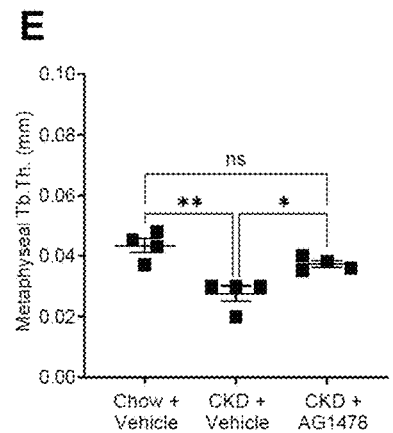
Figure 5F:
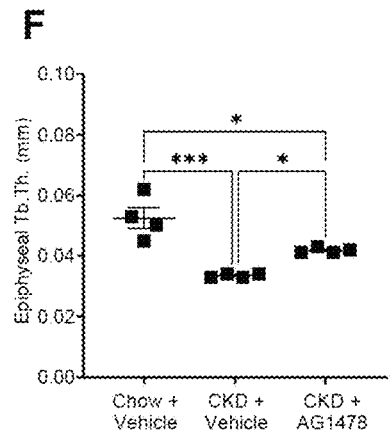
Figure 5G:
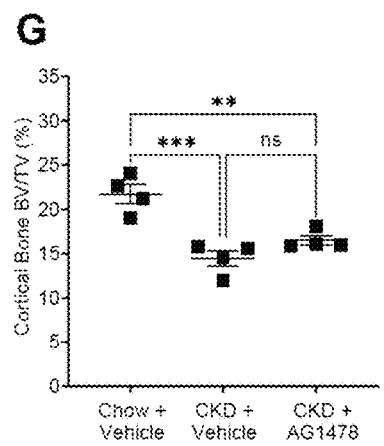
Figure 5H:
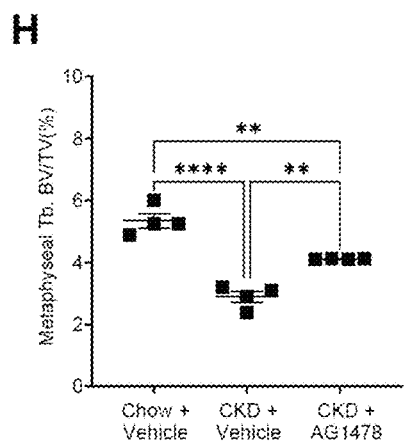
Figure 5I:
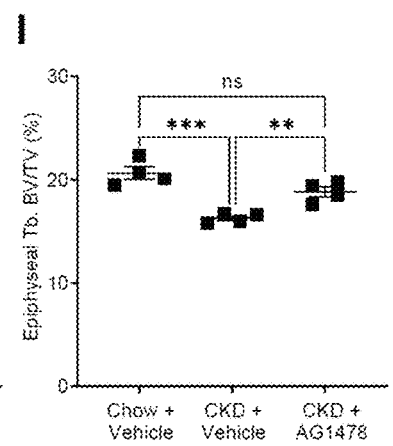

The femurs resected from murine groups were assessed to analyze the effects of EGFR inhibition on bone mineralization (FIGS. 5A-5C). The thickness and bone volume fraction of both trabecular (epiphyseal and metaphysical regions) and cortical bone was significantly reduced in CKD animals compared to chow-fed controls. EGFR inhibition increased the thickness of both trabecular and cortical bone significantly in the CKD mice (p=0.04 and p=0.02 for epiphyseal and metaphysical regions and p=0.004 for cortical bone) (FIGS. 5D-5F). Interestingly, EGFR inhibition increased the bone volume fraction in trabecular bone, both epiphyseal (p=0.009) and metaphysical (p=0.002) regions, compared to CKD animals. However, it did not significantly change in cortical bone (p=0.25) (FIGS. 5G-5I).

The data suggest that osteogenic function of osteoblasts was not affected by EGFR inhibition. Culturing osteoblasts in OS media resulted in the release of TNAP-positive EVs and robust mineralization, neither of which was altered by EGFR inhibition. The observations suggest that, despite many commonalities, bone matrix vesicles and vascular calcifying EVs originate through different mechanisms. CKD patients often exhibit bone disorders, including decreased bone mass density.

The results demonstrated that EGFR inhibition significantly reversed reductions in trabecular and cortical thickness in the CKD mice; bone volume fraction in trabecular regions significantly increased by the treatment, while cortical bone volume fraction was not improved. At the least, these results suggest that EGFR inhibition does not induce deleterious bone remodeling, and may improve CKD-induced bone pathologies.

Example 6—EGFR Inhibition does not Affect CD63 EV Content

Figure 6:
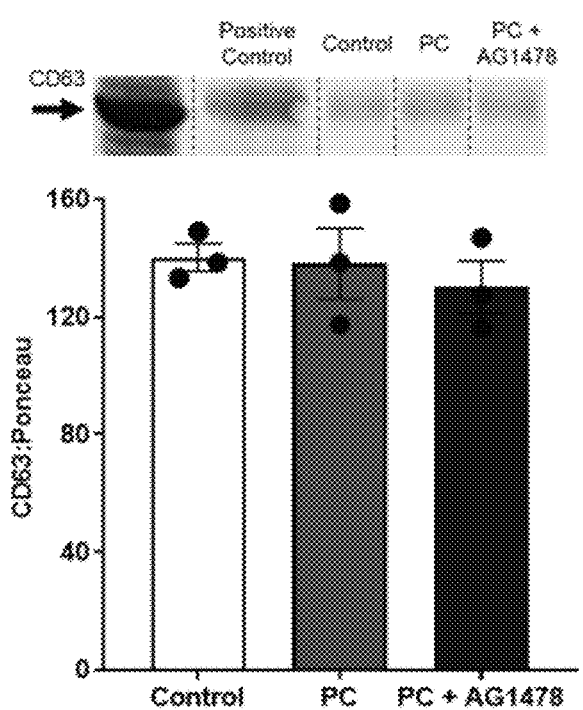
FIG. 6 shows no differences in CD63 in EVs obtained from SMCs cultured in control media, pro-calcific media, or pro-calcific media treated with 2.5 μM. AG1478 for 14 days.

EGFR inhibition disrupts calcifying EV formation. to determine whether the treatment alters other types of EV formation, CD63, a widely utilized marker enriched in exosomes and other EV subtypes was blotted. The data demonstrate no differences in CD63 protein within EVs from vascular SMCs cultured in control media, pro-calcific media (Dulbecco's Modified Eagle Medium supplemented with 10% fetal bovine serum, 1% antibiotic solution, 10 mM β-glycerophosphate, 0.1 mM L-ascorbic acid, and 10 nM dexamethasone), or pro-calcific sample treated with AG1478 (FIG. 6). The data suggest that CD63-positive EV release is not altered by EGFR inhibition.

In summary, the data indicate that CKD-induced vascular calcification associates with increased serum EGFR in mice, and that inhibiting EGFR tyrosine kinase activity prevents vascular calcification in a CKD mouse model, with 100% survival rate. The in vivo results show reduced calcium burden in the aorta of CKD mice treated with EGFR tyrosine kinase inhibitor, AG1478. This effect is independent of kidney remodeling as AG1478 treatment does not reduce the expression of common markers of renal injury. The data also show elevated serum TNAP activity in both CKD mice and CKD mice treated with EGFR inhibitor, demonstrating that EGFR inhibition prevents vascular calcification independent from serum TNAP activity and renal injury.

The results demonstrate elevated CAV1-positive EVs in the aorta of CKD mice, which is reduced by EGFR inhibition. Similarly, TNAP activity is elevated in EVs isolated from the aortae of CKD mice, while EGFR inhibition reduces the activity of this enzyme in the EVs. Calcifying EVs are enriched in Annexin V, a collagen-binding $Ca^{2+}$ channel. The results show that Annexin V is elevated in VSMC EVs, which is also reduced by EGFR inhibition. Taken together, these results suggest that targeting the CAV1-dependent formation of calcifying EVs by EGFR inhibition reduces vascular calcification in the CKD mouse model.

Further, the data suggest that EGFR inhibition does not alter SMC phenotype, but directly affects caveolin-1 trafficking. This provides a unique therapeutic strategy to modulate calcifying EV formation independent of cell phenotype.

All patents and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application

---

What is claimed is:

1. A method for treating vascular calcification comprising administering, to a subject in need of such treatment, a pharmaceutical composition comprising an EGFR inhibitor.

2. The method of claim 1, the vascular calcification being cardiovascular calcification.

3. The method of claim 1, the vascular calcification being medial vascular calcification or intimal atherosclerotic calcification.

4. The method of claim 1, the EGFR inhibitor being selected from monoclonal antibodies and small-molecule tyrosine kinase inhibitors.

5. The method of claim 1, the EGFR inhibitor being selected from necitumumab, saracatinib, canertinib, dacomitinib, vandetanib, neratinib, erlotinib, gefitinib, afatinib, Osimertinib, lapatinib, AG1478, AG490, CP724714, WZ4002, sapitinib, CUDC-101, PD153035, pelitinib, AEE788, AC480, OSI-420, WZ3146, Allitinib, Rociletinib, Varlitinib, Icotinib, TAK-285, WHI-P154, Daphnetin, PD168393, CNX-2006, Tyrphostin 9, AG-18, Epertinib, BI-4020, Tyrphostin AG-528, SU5214, RG 13022, TQB3804, TAS6417, Pyrotinib, PD153035, AG 494, AG 555, Theliatinib, Avitinib, Lazertinib, Lifirafenib, Nazartinib, Brigatinib, Tucatinib, AZD3759, CL-387785, Poziotinib, AZ5104, cetuximab, panitumumab, matuzumab and Mobocertinib.

6. The method of claim 5, the EGFR inhibitor being AG1478.

7. The method of claim 1, the subject being a human.

8. The method of claim 1, the subject having been diagnosed with chronic kidney disease (CKD), diabetes, hyperparathyroidism, hyperphosphatemia, a vitamin D disorder, a vitamin K disorder, osteoporosis, Kawasaki disease, arterial calcification due to deficiency of CD73 (ACDC), idiopathic basal ganglia calcification (IBGC), pseudoxanthoma elasticum (PXE), rheumatoid arthritis, Singleton-Merten syndrome, β-thalassemia, atherosclerosis, hyperlipidemia, hypertension, amputation, congenital bicuspid valve, and/or rheumatic heart disease.

9. The method of claim 1, the subject having been diagnosed with CKD.

10. The method of claim 1, the administration being local, oral, transdermal, parenteral, or intraarticular administration.

11. The method of claim 10, the administration being local, oral, transdermal, or parenteral; administration.

12. A method for reducing mineral nucleation and deposition in a vascular wall, the method comprising administering, to a subject in need of such reduction, a pharmaceutical composition comprising an EGFR inhibitor.

13. The method of claim 12, the EGFR inhibitor being selected from monoclonal antibodies and small-molecule tyrosine kinase inhibitors.

14. The method of claim 12, the EGFR inhibitor being selected from necitumumab, saracatinib, canertinib, dacomitinib, vandetanib, neratinib, erlotinib, gefitinib, afatinib, Osimertinib, lapatinib, AG1478, AG490, CP724714, WZ4002, sapitinib, CUDC-101, PD153035, pelitinib, AEE788, AC480, OSI-420, WZ3146, Allitinib, Rociletinib, Varlitinib, Icotinib, TAK-285, WHI-P154, Daphnetin, PD168393, CNX-2006, Tyrphostin 9, AG-18, Epertinib, BI-4020, Tyrphostin AG-528, SU5214, RG 13022, TQB3804, TAS6417, Pyrotinib, PD153035, AG 494, AG 555, Theliatinib, Avitinib, Lazertinib, Lifirafenib, Nazartinib, Brigatinib, Tucatinib, AZD3759, CL-387785, Poziotinib, AZ5104, cetuximab, panitumumab, matuzumab and Mobocertinib.

15. The method of claim 12, the subject being a human having been diagnosed with CKD or atherosclerosis.

16. The method of claim 14, the EGFR inhibitor being AG1478.

17. A method for treating chronic kidney disease (CKD) or atherosclerosis by reducing mineral nucleation and deposition in a vascular wall, the method comprising administering, to a subject in need of such reduction, a pharmaceutical composition comprising an EGFR inhibitor.

18. The method of claim 17, the EGFR inhibitor being selected from necitumumab, saracatinib, canertinib, dacomitinib, vandetanib, neratinib, erlotinib, gefitinib, afatinib, Osimertinib, lapatinib, AG1478, AG490, CP724714, WZ4002, sapitinib, CUDC-101, PD153035, pelitinib, AEE788, AC480, OSI-420, WZ3146, Allitinib, Rociletinib, Varlitinib, Icotinib, TAK-285, WHI-P154, Daphnetin, PD168393, CNX-2006, Tyrphostin 9, AG-18, Epertinib, BI-4020, Tyrphostin AG-528, SU5214, RG 13022, TQB3804, TAS6417, Pyrotinib, PD153035, AG 494, AG 555, Theliatinib, Avitinib, Lazertinib, Lifirafenib, Nazartinib, Brigatinib, Tucatinib, AZD3759, CL-387785, Poziotinib, AZ5104, cetuximab, panitumumab, matuzumab and Mobocertinib.

19. The method of claim 18, the EGFR inhibitor being AG1478.

20. The method of claim 17, the administration being local, oral, transdermal, parenteral, or intraarticular administration.

* * * * *

SEQUENCE LISTING

```
<160> NUMBER OF SEQ ID NOS: 14

<210> SEQ ID NO 1
<211> LENGTH: 25
<212> TYPE: DNA
<213> ORGANISM: Artificial sequence
<220> FEATURE:
<223> OTHER INFORMATION: primer

<400> SEQUENCE: 1
cttcgctctc tgctcctcct gttcg                                              25

<210> SEQ ID NO 2
<211> LENGTH: 24
<212> TYPE: DNA
<213> ORGANISM: Artificial sequence
<220> FEATURE:
<223> OTHER INFORMATION: primer

<400> SEQUENCE: 2
accaggcgcc caatacgacc aaat                                               24

<210> SEQ ID NO 3
<211> LENGTH: 22
<212> TYPE: DNA
<213> ORGANISM: Artificial sequence
<220> FEATURE:
<223> OTHER INFORMATION: primer

<400> SEQUENCE: 3
gctctctaac cacagtctat gc                                                 22

<210> SEQ ID NO 4
<211> LENGTH: 20
<212> TYPE: DNA
<213> ORGANISM: Artificial sequence
<220> FEATURE:
<223> OTHER INFORMATION: primer

<400> SEQUENCE: 4
aggctgtttg atgccatagt                                                    20

<210> SEQ ID NO 5
<211> LENGTH: 23
<212> TYPE: DNA
<213> ORGANISM: Artificial sequence
<220> FEATURE:
<223> OTHER INFORMATION: primer

<400> SEQUENCE: 5
ggagtatgag agtgacgaga aag                                                23

<210> SEQ ID NO 6
<211> LENGTH: 21
```

```
<212> TYPE: DNA
<213> ORGANISM: Artificial sequence
<220> FEATURE:
<223> OTHER INFORMATION: primer

<400> SEQUENCE: 6
gaagtgggag tgcttgtatc t                                              21

<210> SEQ ID NO 7
<211> LENGTH: 19
<212> TYPE: DNA
<213> ORGANISM: Artificial sequence
<220> FEATURE:
<223> OTHER INFORMATION: primer

<400> SEQUENCE: 7
tcacactcct cgccctatt                                                 19

<210> SEQ ID NO 8
<211> LENGTH: 20
<212> TYPE: DNA
<213> ORGANISM: Artificial sequence
<220> FEATURE:
<223> OTHER INFORMATION: primer

<400> SEQUENCE: 8
cctcctgctt ggacacaaaa                                                20

<210> SEQ ID NO 9
<211> LENGTH: 18
<212> TYPE: DNA
<213> ORGANISM: Artificial sequence
<220> FEATURE:
<223> OTHER INFORMATION: primer

<400> SEQUENCE: 9
aacgacccct tcattgac                                                  18

<210> SEQ ID NO 10
<211> LENGTH: 19
<212> TYPE: DNA
<213> ORGANISM: Artificial sequence
<220> FEATURE:
<223> OTHER INFORMATION: primer

<400> SEQUENCE: 10
tccacgacat actcagcac                                                 19

<210> SEQ ID NO 11
<211> LENGTH: 22
<212> TYPE: DNA
<213> ORGANISM: Artificial sequence
<220> FEATURE:
<223> OTHER INFORMATION: primer

<400> SEQUENCE: 11
cctcagggta ttgctggaca ac                                             22

<210> SEQ ID NO 12
<211> LENGTH: 23
<212> TYPE: DNA
<213> ORGANISM: Artificial sequence
<220> FEATURE:
<223> OTHER INFORMATION: primer

<400> SEQUENCE: 12
```

-continued

```
accacttgat ccagaaggac ctt                                              23

<210> SEQ ID NO 13
<211> LENGTH: 20
<212> TYPE: DNA
<213> ORGANISM: Artificial sequence
<220> FEATURE:
<223> OTHER INFORMATION: primer

<400> SEQUENCE: 13
tggagcaaca tgtggaactc                                                  20

<210> SEQ ID NO 14
<211> LENGTH: 18
<212> TYPE: DNA
<213> ORGANISM: Artificial sequence
<220> FEATURE:
<223> OTHER INFORMATION: primer

<400> SEQUENCE: 14
cagcagccgg ttaccaag                                                    18
```